(12) United States Patent
Gonnelli et al.

(10) Patent No.: US 7,931,614 B2
(45) Date of Patent: Apr. 26, 2011

(54) INJECTION SYSTEMS

(75) Inventors: Robert R. Gonnelli, Mahwah, NJ (US); David Lipson, No. Andover, MA (US); Vasu Nishtala, Westford, MA (US); Ciro Dimeglio, Shrewsbury, MA (US)

(73) Assignee: Valeritas, Inc., Bridgewater, NJ (US)

( * ) Notice: Subject to any disclaimer, the term of this patent is extended or adjusted under 35 U.S.C. 154(b) by 647 days.

(21) Appl. No.: 10/001,002

(22) Filed: Nov. 30, 2001

(65) Prior Publication Data
US 2003/0149397 A9    Aug. 7, 2003

Related U.S. Application Data

(60) Provisional application No. 60/250,410, filed on Nov. 30, 2000, provisional application No. 60/250,425, filed on Nov. 30, 2000, provisional application No. 60/250,537, filed on Nov. 30, 2000, provisional application No. 60/250,573, filed on Nov. 30, 2000.

(51) Int. Cl.
*A61M 5/30* (2006.01)
*A61M 37/00* (2006.01)

(52) U.S. Cl. .................. 604/68; 604/70; 604/86
(58) Field of Classification Search .......... 604/69, 604/140–141, 143, 145, 82, 87–91, 68, 48, 604/86, 70, 83
See application file for complete search history.

(56) References Cited

U.S. PATENT DOCUMENTS

| | | | |
|---|---|---|---|
| 2,653,604 A | 9/1953 | Hein, Jr. | |
| 3,785,379 A * | 1/1974 | Cohen | 128/218 |
| 3,802,430 A * | 4/1974 | Schwebel et al. | 604/69 |
| 4,059,107 A | 11/1977 | Iriguchi et al. | |
| 4,059,109 A | 11/1977 | Tischlinger | |
| 4,652,261 A | 3/1987 | Mech et al. | |
| 4,928,571 A | 5/1990 | Bulman | |
| 4,945,809 A | 8/1990 | Bulman et al. | |
| 5,116,313 A | 5/1992 | McGregor | |
| 5,281,198 A * | 1/1994 | Haber et al. | 604/86 |
| 5,421,264 A | 6/1995 | Petrick | |
| 5,454,786 A * | 10/1995 | Harris | 604/88 |
| 5,499,972 A | 3/1996 | Parsons | |
| 5,503,627 A | 4/1996 | McKinnon et al. | |
| 5,503,628 A | 4/1996 | Fetters et al. | |
| 5,520,639 A | 5/1996 | Peterson et al. | |
| 5,527,288 A | 6/1996 | Gross et al. | |
| 5,538,503 A | 7/1996 | Henley | |

(Continued)

FOREIGN PATENT DOCUMENTS
EP    0331855    8/1995
(Continued)

*Primary Examiner* — Nicholas D Lucchesi
*Assistant Examiner* — Brooke M Matney
(74) *Attorney, Agent, or Firm* — Morgan, Lewis & Bockius LLP

(57) ABSTRACT

The invention in general relates to various injection systems and devices that can be used, for example, in needleless injection systems for human, and for domestic and farm animals. In certain embodiments, the invention provides an injection system comprising: an injector defining a first cavity in fluid communication with an orifice configured for needleless injection; a housing defining a second cavity, the housing different than the injector; a first movable member between the first cavity and the second cavity, wherein the first movable member is configured to transfer a fluid from the second cavity to the first cavity; and wherein the first movable member is configured to be substantially stationary until the first movable member is moved by a propellant.

21 Claims, 21 Drawing Sheets

U.S. PATENT DOCUMENTS

| | | |
|---|---|---|
| 5,569,189 A | 10/1996 | Parsons |
| 5,599,302 A | 2/1997 | Lilley et al. |
| 5,607,418 A | 3/1997 | Arzbaecher |
| 5,616,132 A | 4/1997 | Newman |
| 5,618,269 A | 4/1997 | Jacobsen et al. |
| 5,649,912 A | 7/1997 | Peterson |
| 5,658,247 A | 8/1997 | Henley |
| 5,685,846 A | 11/1997 | Michaels, Jr. |
| 5,693,017 A | 12/1997 | Spears et al. |
| 5,704,911 A | 1/1998 | Parsons |
| 5,730,723 A | 3/1998 | Castellano et al. |
| 5,746,714 A | 5/1998 | Salo et al. |
| 5,782,802 A | 7/1998 | Landau |
| 5,814,020 A | 9/1998 | Gross |
| 5,836,915 A | 11/1998 | Steinbach et al. |
| 5,846,233 A | 12/1998 | Lilley et al. |
| 5,851,198 A | 12/1998 | Castellano et al. |
| 5,858,001 A | 1/1999 | Tsals et al. |
| 5,860,957 A | 1/1999 | Jacobsen et al. |
| 5,891,085 A | 4/1999 | Lilley et al. |
| 5,891,086 A | 4/1999 | Weston |
| 5,893,397 A | 4/1999 | Peterson et al. |
| 5,919,159 A | 7/1999 | Lilley et al. |
| 5,936,514 A | 8/1999 | Anderson et al. |
| 5,938,637 A | 8/1999 | Austin et al. |
| 5,947,928 A | 9/1999 | Muller |
| 5,957,895 A | 9/1999 | Sage et al. |
| 5,993,412 A | 11/1999 | Deily et al. |
| 6,045,534 A | 4/2000 | Jacobsen et al. |
| 6,056,724 A | 5/2000 | Lacroix |
| 6,063,053 A | 5/2000 | Castellano et al. |
| 6,074,360 A | 6/2000 | Haar et al. |
| 6,096,002 A * | 8/2000 | Landau ............... 604/68 |
| 6,099,504 A | 8/2000 | Gross et al. |
| 6,132,395 A | 10/2000 | Landau et al. |
| 6,165,155 A | 12/2000 | Jacobsen et al. |
| 6,258,062 B1 | 7/2001 | Thielen et al. |
| 6,258,063 B1 * | 7/2001 | Haar et al. ............ 604/141 |
| 6,270,473 B1 | 8/2001 | Schwebel |
| 6,319,224 B1 | 11/2001 | Stout et al. |
| 6,406,455 B1 * | 6/2002 | Willis et al. ............ 604/68 |
| 6,537,245 B1 * | 3/2003 | Alexandre et al. ......... 604/69 |
| 6,592,545 B1 | 7/2003 | Bellhouse et al. |
| 6,708,621 B1 | 3/2004 | Forichon-Chaumet et al. |
| 6,740,062 B2 | 5/2004 | Hjertman |
| 6,758,829 B2 | 7/2004 | Alexandre et al. |
| 6,830,560 B1 | 12/2004 | Gross et al. |
| 6,835,187 B2 | 12/2004 | Alexandre et al. |
| 6,881,200 B2 | 4/2005 | Bellhouse et al. |
| 2001/0027290 A1 | 10/2001 | Weston |
| 2001/0027293 A1 | 10/2001 | Joshi |
| 2002/0004639 A1 | 1/2002 | Willis et al. |
| 2002/0035348 A1 | 3/2002 | Hjertman |

FOREIGN PATENT DOCUMENTS

| | | |
|---|---|---|
| WO | WO 95/24176 | 9/1995 |
| WO | WO-98/28029 | 7/1998 |
| WO | WO 99/21609 | 5/1999 |
| WO | WO 00/10630 | 3/2000 |
| WO | WO 00/15281 A1 * | 3/2000 |
| WO | WO-00/35520 | 6/2000 |
| WO | WO 00/48654 | 8/2000 |
| WO | WO 01/05451 | 1/2001 |
| WO | WO 01/05452 | 1/2001 |
| WO | WO 01/13975 | 3/2001 |
| WO | WO 01/78810 A1 | 10/2001 |

\* cited by examiner

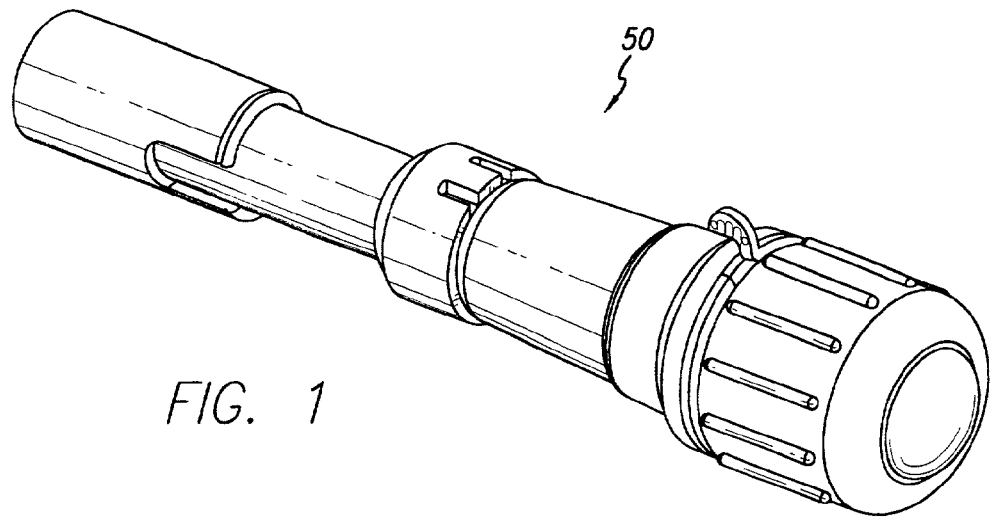
FIG. 1
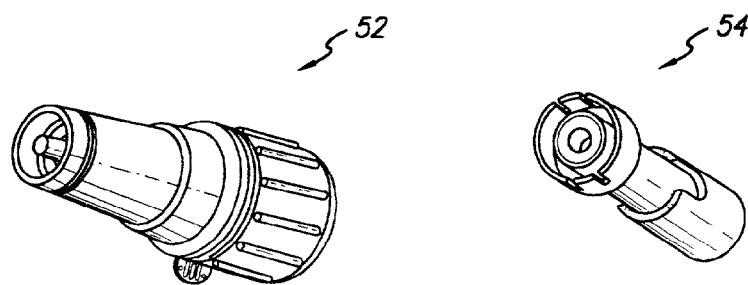
FIG. 2
FIG. 3

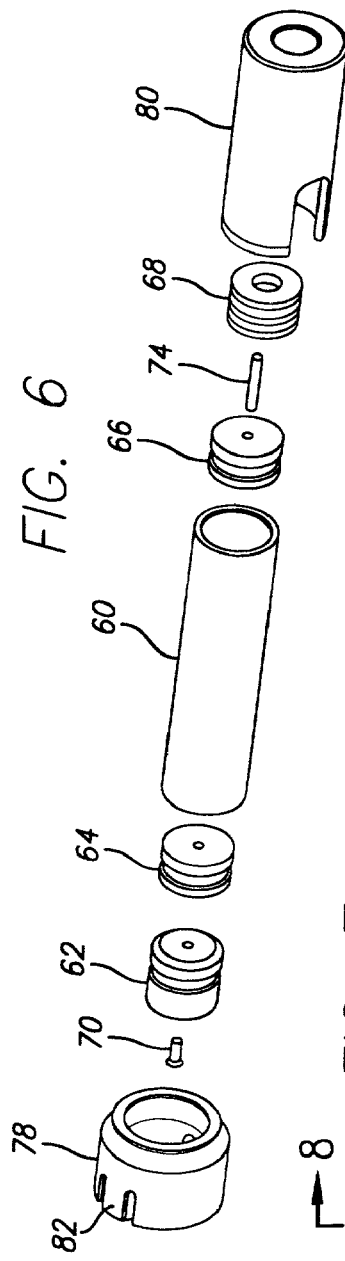
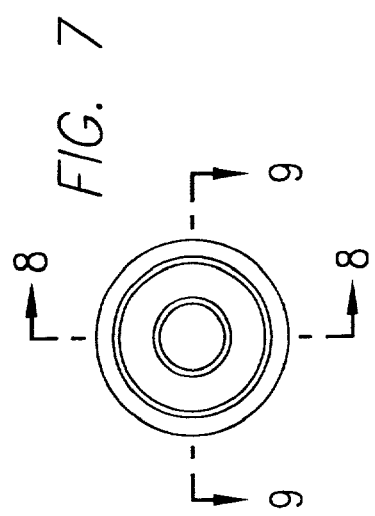
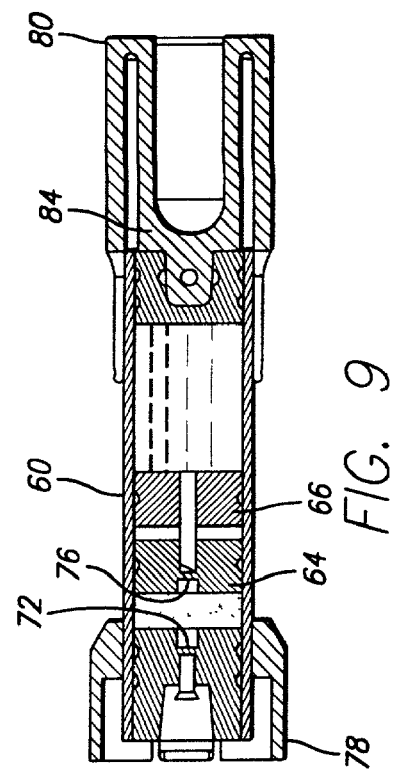
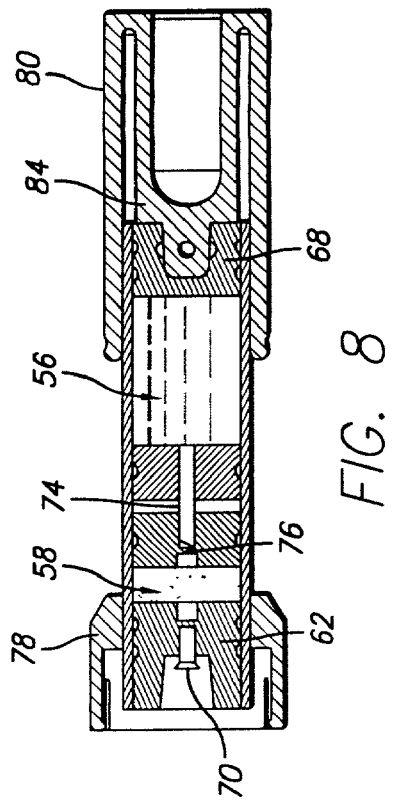
FIG. 6
FIG. 7
FIG. 8
FIG. 9

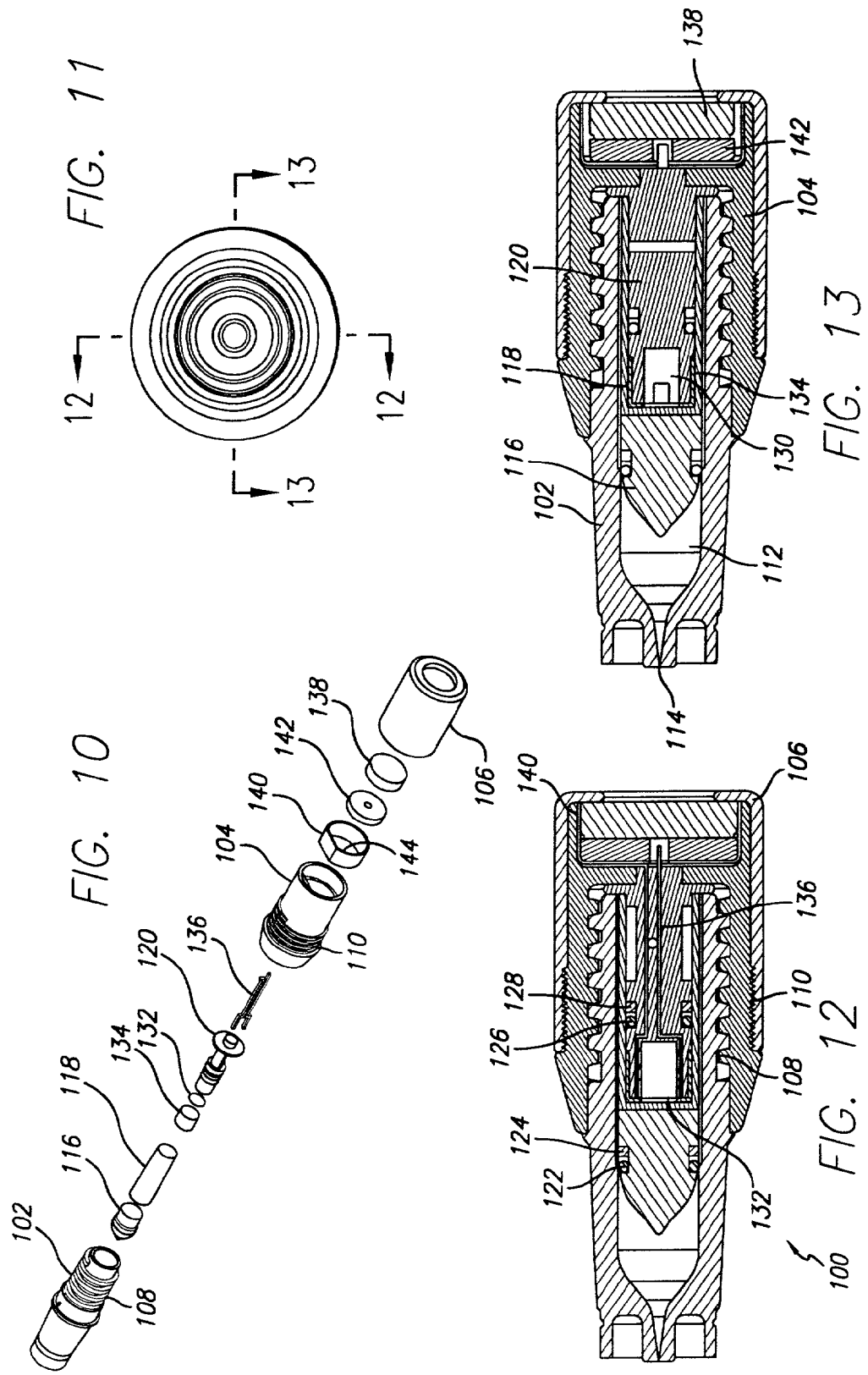

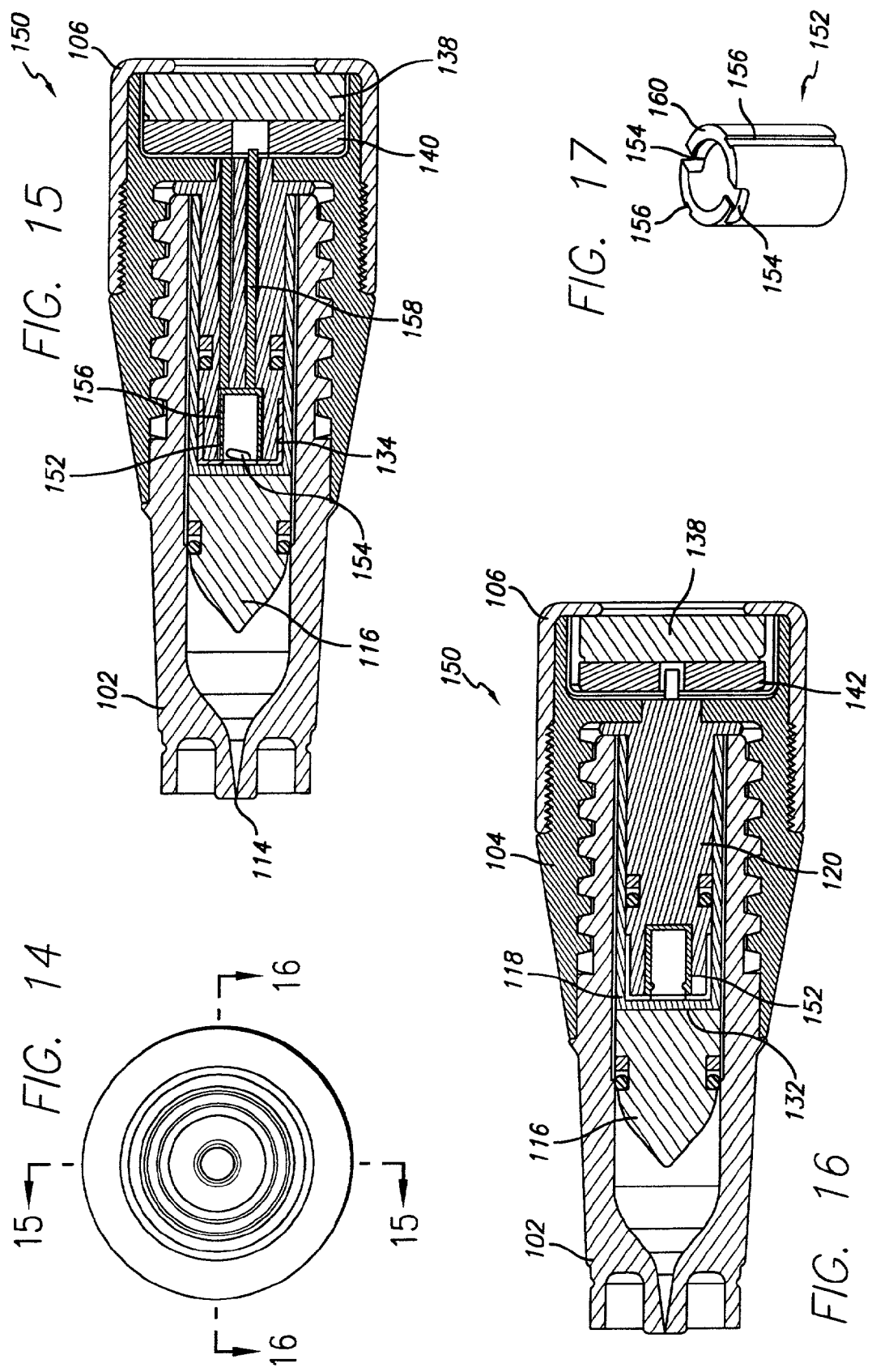

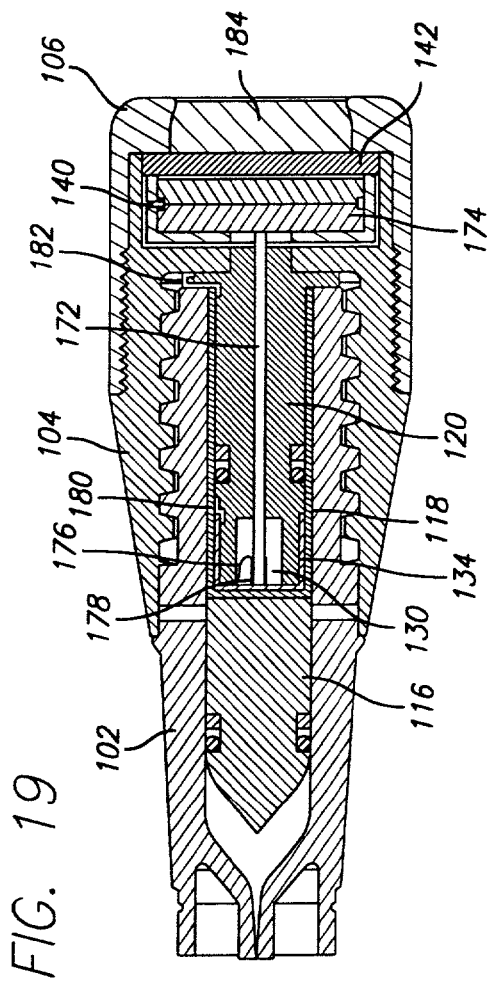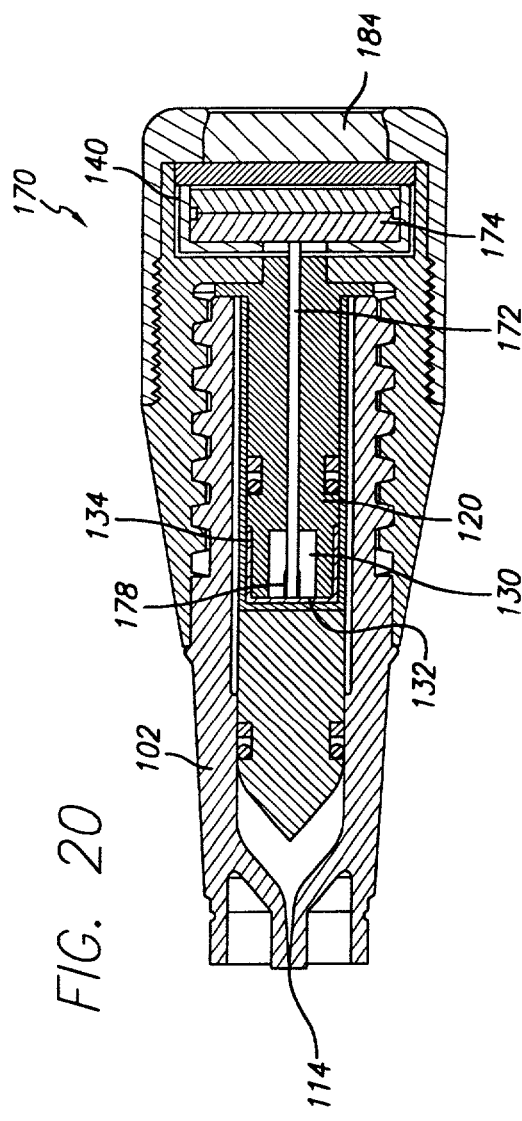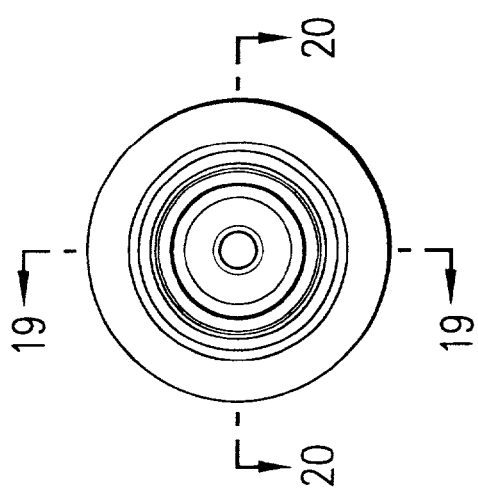

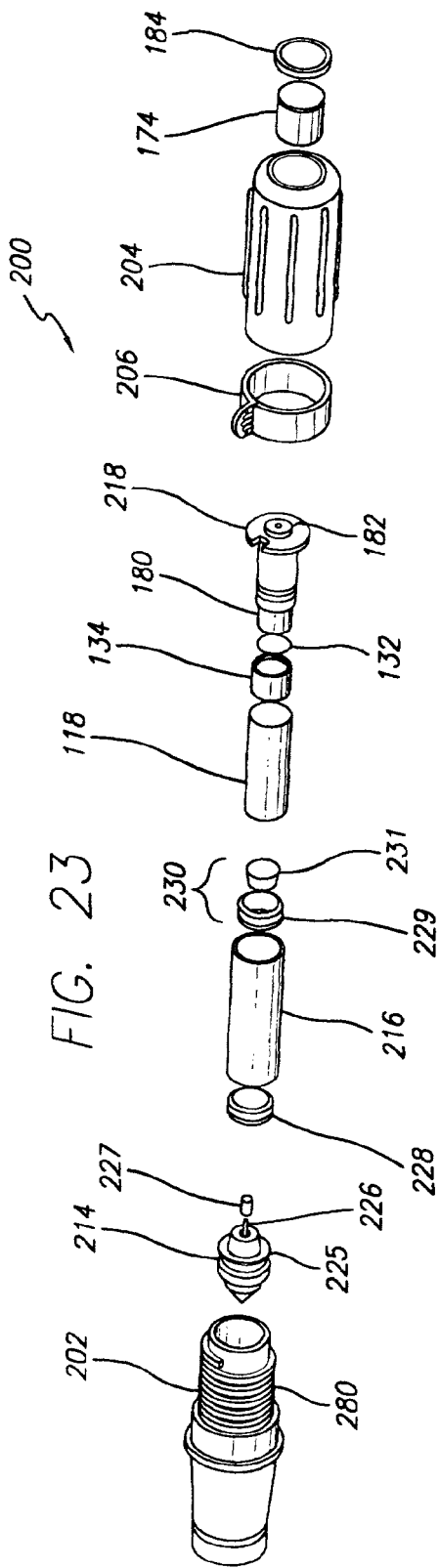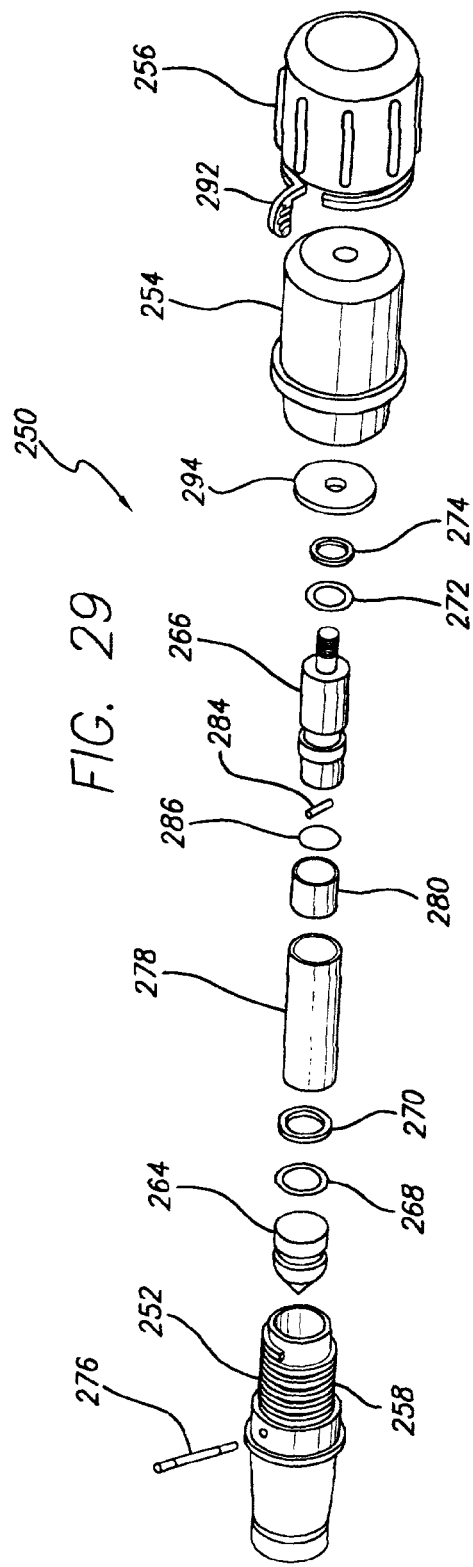

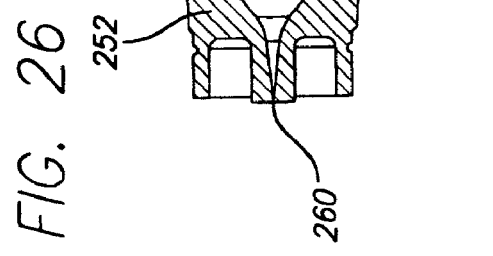
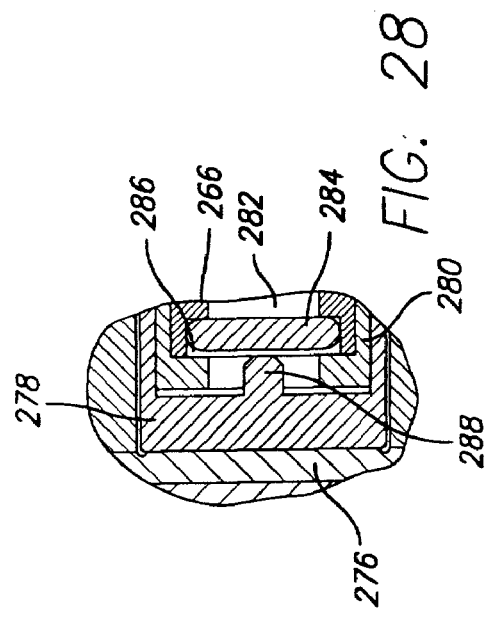
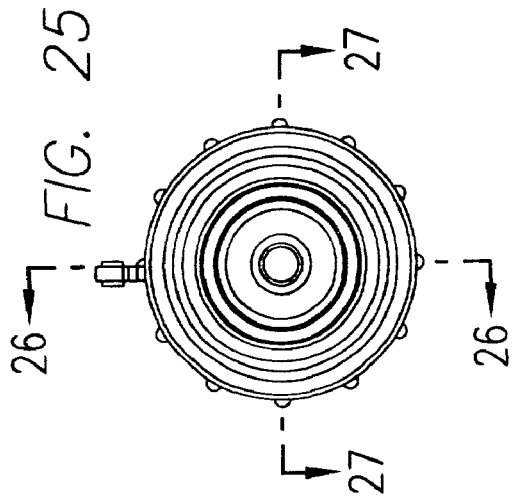
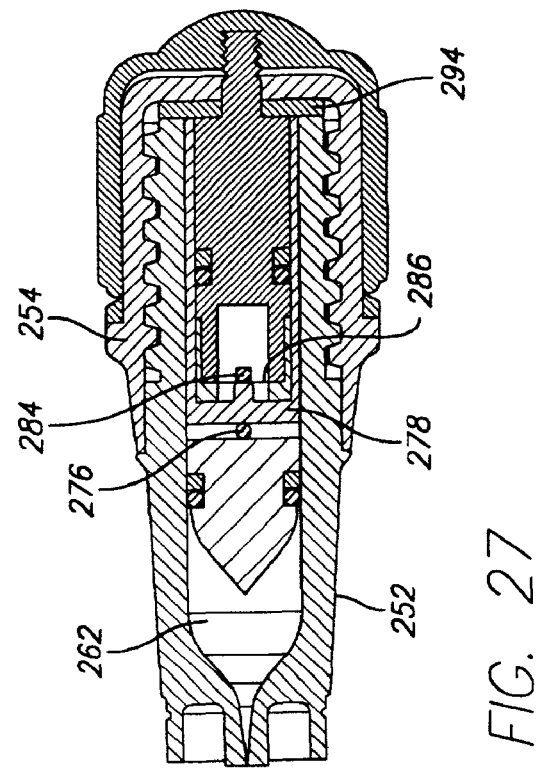

1/2

INJECTION SYSTEMS

CLAIM OF PRIORITY

This application claims priority under 35 USC §119(e) to U.S. Provisional Patent Application Ser. Nos. 60/250,410; 60/250,425; 60/250,537; and 60/250,573, all filed on Nov. 30, 2000, and all entitled "Injection Devices", the entire contents of which are all hereby incorporated by reference.

FIELD OF THE INVENTION

The invention relates to injection systems and devices that can be used in injection systems.

BACKGROUND

Injection devices can be used for injecting fluids, such as drugs, into a body. Some injection devices, such as needleless injection devices, inject fluids by delivering the fluids at a pressure sufficient to create and to sustain in the body an opening through which the fluids are delivered. A needleless injection device can generate sufficient pressure, for example, by using a compressed gas or a propellant that generates a gas.

SUMMARY

The invention relates to injection systems and devices that can be used in injection systems.

In one aspect, the invention features an injection system including an injector defining a first cavity in fluid communication with an orifice configured for needleless injection, and a housing inside the injector and defining a second cavity, the housing different than the injector, wherein the injection system is configured to transfer a fluid from the second cavity to the first cavity.

Embodiments include one or more of the following features. The injector is formed of a first material, e.g., a polymer, and the housing is formed of a second material, e.g., a glass, different than the first material. The system further includes a first movable member between the first cavity and the second cavity. The first movable member defines a lumen. The system further includes a second movable member between the first movable member and the second cavity.

The first movable member can be configured to engage with the second movable member such that the first cavity is in fluid communication with the second cavity. The first movable member can be configured to be substantially stationary until the first movable member is moved by a propellant of the injection system. The first movable member can include a tab configured to separate from the first movable member at a predetermined force. The tab can engage with the injector.

The injector and the housing can be substantially coaxial.

The second cavity can be defined by the housing and two movable members. The second cavity can be defined by the housing and a movable member. The movable member can be formed of two different materials The movable member can include a rubber.

The system can further include an injector cap connectable to the injector, the injector cap configured to move distally to transfer the fluid from the second cavity to the first cavity. The injector cap can be connectable to the injector by a threaded connection.

The system can further include a charge cup in the injector. The system can further include a charge in the charge cup. The charge can include at least two discrete materials, which can have different combustion characteristics.

In another aspect, the invention features a method including providing an injection system having an injector defining a first cavity in fluid communication with an orifice configured for needleless injection, and a housing inside the injector and defining a second cavity, the housing being different than the injector, and reducing the volume of the second cavity to transfer a fluid from the second cavity to the first cavity.

Embodiments include one or more of the following features. The method further includes flowing the fluid through a movable member between the first and second cavities. The method further includes piercing a member between the first and second cavities. The injection system further includes an injector cap connectable to the injector, and reducing the volume comprises moving the injector cap toward the orifice. Moving the injector cap can include twisting the injector cap. The method can further include moving the fluid through the orifice charge.

The charge can include at least two discrete materials. The at least two discrete materials can have different combustion characteristics.

In another aspect, the invention features an injection system including an injector defining a first cavity in fluid communication with an orifice configured for needleless injection, a movable member in the first cavity, the movable member defining a second cavity, and a charge in the second cavity.

Embodiments include one or more of the following features. The second cavity is at a proximal end of the movable member. The system further includes an electrically conductive member extending at least partially across the charge, the electrically conductive member capable of being in electrical communication with a power source. The system further includes a power unit connectable to the injector. The power unit includes a battery.

The system can further include a membrane at least partially extending across an opening of the second cavity. The system can further include a first electrically conductive portion connected to the movable member. The system can further include a second electrically conductive portion extending through the injector, the second electrically conductive portion in electrical communication with the first electrically conductive portion and capable of being in electrical communication with a power source.

The charge can include at least two discrete materials. The at least two discrete materials can have different combustion characteristics.

At least a portion of the injector can be disposable.
The power unit can be reusable.
The injector can include a needleless injector.
The moveable member can include a piston.

In another aspect, the invention features a method of injection including activating a charge in a movable member disposed in an injector defining an orifice configured for needleless injection.

Embodiments include one or more of the following features. Activating the charge includes flowing electrical current through the charge. The charge is disposed in a cavity defined by the movable member. The cavity is formed at a proximal end of the movable member. The charge includes at least two discrete materials, which can have different combustion characteristics.

In another aspect, the invention features an injection device including an injector defining a first cavity and an orifice, a movable member in the first cavity, a housing defining a second cavity proximal of the movable member, and a charge in the second cavity, the charge including at least two discrete materials.

Embodiments include one or more of the following features. The discrete materials have different combustion characteristics. The charge includes at least two layers of materials, which can be adjacent each other. The charge includes at least one trigger. The charge includes at least one propellant. The charge includes at least one passive decay material. The charge can be electrically activated.

The device can further include an electrically conductive member at least partially extending across the charge.

The movable member and the housing can be integrally formed.

The device can be configured for needleless injection.

The device can include a needleless injector.

In another aspect, the invention features a method including igniting a charge in an injector having an orifice so that a fluid in a cavity in the injector is ejected out of the cavity, wherein the charge includes at least two discrete materials.

Embodiments include one or more of the following features. The injector orifice is configured for needleless injection. The injector includes a needleless injector. The method further includes selecting the at least two discrete materials so that the fluid is ejected from the cavity in a predetermined fashion.

Embodiments can include one or more of the following advantages. The injection systems include injector devices that are resistant to stresses from internal injection pressures produced in the devices. Therefore, the risk of an unreliable injection and/or the risk of danger to the user can be minimized. In embodiments, the injection pressures are transmitted directly to a member, e.g., a piston, expelling the fluids such that the fluids are injected predictably, e.g., few, if any, no harmonics in an injection pressure curve.

In embodiments, the injection devices contain injectable fluids in a housing that is relatively inert to the injectable fluids. For example, the housing can be made of standard, pharmacologically-acceptable materials, such as glass or a polymer. Therefore, the fluids can be maintained efficacious and be delivered safely and effectively.

The injection devices feature a modular, self-contained configuration having a compact, low profile. The injection devices are also easy-to-use, relatively low cost to manufacture, and disposable.

In some embodiments, the injection systems feature an injectable material housing having a relatively small diameter, which can provide for efficient filling during production, e.g., by allowing more housings to be placed in a manufacturing tray. The design of the housing can also provide a mechanical advantage so that the device is relatively easy to use.

Embodiments involving a multi-stage charge can exhibit any of numerous advantages. As an example, multiple pyrotechnic materials with different burning characteristics can be used in numerous combinations (sequence, stoichiometry, charge shape, particle shape and size, etc) to provide a desired pressure profile. As another example, the thrust and performance of the charge can be stable and predictable. As a further example, the charge can be relatively leak-proof, simple and inexpensive. As an additional example, the charge can be relatively insensitive to external temperatures. As another example, the charge has a relatively long shelf life.

In some embodiments, the injection devices include an injector that is resistant to stresses from an internal injection pressure produced in the devices. Therefore, the risk of an unreliable injection and/or the risk of danger to the user can be minimized. In some embodiments, the injection pressure is transmitted directly to a member expelling the fluids, e.g., a piston, such that the fluids are injected predictably, e.g., having no harmonics in an injection pressure curve.

In some embodiments, the injection devices contain injectable fluids in a housing that is relatively inert to the injectable fluids. For example, the housing can be made of standard, pharmacologically-acceptable materials, such as glass or a polymer. Therefore, the fluids can be maintained efficacious and be delivered safely and effectively.

The injection devices feature a modular, self-contained configuration having a compact, low profile. The injection devices are also easy-to-use, relatively low cost to manufacture, and disposable.

In some embodiments, the injection devices feature an injectable material housing having a relatively small diameter, which can provide for efficient filling during production, e.g., by allowing more housings to be placed in a manufacturing tray. The design of the housing can also provide a mechanical advantage so that the device is relatively easy to use.

In general, the invention features an injection device. The device includes: a first housing formed of a first material and configured to house an injectable material; a second housing defining an orifice, which is preferably configured for needleless injections, the second housing formed of a second material different than the first material, the first and second housings configured to mate together wherein the first housing is capable of transferring the injectable material to the second housing, preferably through the orifice that will be used for injection; and a propellant in the second housing, the propellant, e.g., a chemical propellant, configured to displace the injectable material through the orifice and out of the second housing.

In a preferred embodiment, the injectable material is delivered to the injector by way of the orifice, which is the same orifice used to inject or to deliver the injectable material.

In a preferred embodiment, the device includes a first housing having an injectable material and a second housing having a propellant, e.g., a chemical propellant. The first housing can be configured such that it is detached or left attached to the second housing prior to injection. The second housing can be proximal to the first housing when used. In a preferred embodiment, the housings are configured such that, upon mating, a slidable member, e.g., a piston or a stopper, of the first housing can be displaced, e.g., in the direction of the second housing, to transfer injectable material from the first housing to the second housing. The second housing can be configured such that it slides into the first housing. In other embodiments, the device includes a third member that displaces a moveable element of the first housing, e.g., the third housing can slide into or over the first housing.

In a preferred embodiment, the second material: is more break-resistant than the first material; comprises a material that breaks non-catastrophically; comprises a polymer, e.g., polycarbonate.

In a preferred embodiment, the first material is chemically inert to the injectable material over a shelf life of the injectable material, e.g., a glass or a polymer.

In a preferred embodiment, the propellant comprises a chemical pyrotechnic material. The propellant can be disposed on a moveable element, e.g., in a movable sleeve. This allows the moveable element to be displaced from a first position before injection to a second position after injection.

The second housing can comprise a bypass portion and/or a lyophilized material, e.g., a protein, in the second housing. The second housing further can define a bypass channel configured for transferring the injectable material from the first housing to the second housing.

The first housing can comprise two members comprising a resilient and/or compressible material, e.g., butylene rubber and the injectable material can be housed between the members.

The first and second housings can be configured to transfer and/or to deliver the injectable material through the orifice.

In another aspect, the invention features an injection device, comprising: a first housing formed of a first material, e.g., a polymer such as polycarbonate, and defining an orifice configured for needleless injection; a second housing formed of a second material, e.g., glass, different than the first material and configured to house an injectable material, the second housing further configured to mate with the first housing and to transfer the injectable material to the first housing; and a third housing configured to mate with the second housing and to generate a pressure in the first housing.

Embodiments may include one or more of the following features. The first material comprises polycarbonate. The first housing defines a bypass channel configured to transfer the injectable material from the second housing to the first housing. The injection device further comprises a lyophilized material contained in the first housing. The second housing comprises an outer member formed of a third material that can be different than the second material. The third material comprises polycarbonate. The second housing comprises a resilient material, e.g., a butylene rubber member. The third housing comprises a chemical pyrotechnic material configured to generate the pressure in the first housing. The third housing comprises a movable piston. The third housing comprises a member extending from an end of the third housing to the first housing when the first, second and third housings are fully mated, and the member comprises a movable piston and a chemical pyrotechnic material.

In another aspect, the invention features a method of using an injection device, the method comprising: transferring an injectable material from a first housing formed of a first material to a second housing formed of a second material, the second material being different than the first material; and injecting the injectable material by producing a pyrotechnic reaction in the second housing.

Embodiments may include one or more of the following features. Transferring the injectable material comprises engaging the second housing with the first housing. The method further comprises disengaging the first housing from the second housing. Transferring the injectable material comprises flowing the injectable material through a bypass channel.

In another aspect, the invention features an injector, comprising: a housing having a distal end and a proximal end, the housing defining an orifice configured for needleless injection at the distal end; a movable member in the housing; and a propellant assembly configured to mate with the proximal end of the housing, wherein the injector is configured to receive an injectable material through the orifice.

Embodiments may include one or more of the following features. The housing is configured to mate with a second housing containing the injectable material from the distal end of the housing. The housing is formed of a material comprising polycarbonate. The housing further defines a bypass channel. The propellant assembly is configured to propel a second movable member using a pyrotechnic reaction. The movable member is adjacent to the second movable member.

In yet another aspect, the invention features housing, comprising: a vial having a first end and a second end; a first stopper disposed at the first end; and a second stopper disposed at the second end, wherein the vial and the first and second stoppers are configured to house an injectable material. The second stopper is configured to be movable in the vial under an applied pressure.

Embodiments may include one or more of the following features. The vial is formed of a glass. The first and second stoppers, e.g., formed of a butylene rubber, are configured to be engageable. The first and/or second stopper comprises a breakable seal.

In yet another aspect, the invention features an injection device, comprising: a first housing formed of a first material and defining an orifice, the first housing having a propellant, preferably a chemical propellant, therein; a second housing formed of a second material different than the first material and configured to house an injectable material, the second housing having a first end and a second end, wherein the first end is engageable with the orifice; and a member configured to be engageable with the second end, wherein, when the first and second housings are engaged and the second housing and the member are engaged, the device is configured to transfer the injectable material from the second housing through the orifice to the first housing, and the propellant, e.g., a chemical propellant, is configured to displace the injectable material from the first housing through the orifice.

Embodiments may contain one or more of the following features. The orifice is configured for needleless injection. The first end comprises a hollow pin. The first end comprises a butylene member affixed to the first end of the second housing. The second end comprises a member moveable within the second housing. The member composes a sleeve having a closed end, the member extending from the closed end.

In another aspect, the invention features a method of using an injection device, the method comprising: providing the injection device comprising: a first housing formed of a first material and defining an orifice, the first housing having a propellant therein; a second housing formed of a second material different than the first material and configured to house an injectable material, the second housing having a first end and a second end, wherein the first end is engageable with the orifice; and a member configured to be engageable with the second end; engaging the member with the second end; engaging the orifice with the first end; and moving the second housing and the member together, wherein the injectable material can be transferred from the second housing to the first housing.

Embodiments may contain one or more of the following features. Engaging the orifice with the first end comprises breaking a seal. The first end comprises a resilient material, e.g., a butylene member having a hollow pin, and engaging the orifice with the first end comprises moving the pin to break a seal on the butylene member. The member composes a sleeve having a closed end, the member extending from the closed end, and moving the second housing and the member together comprises moving the second housing coaxially into the sleeve. The method further comprises engaging a charge head with the first housing.

In another aspect, the invention features a method of using a needleless injection device comprising: providing a first housing defining an orifice configured for needleless injection; transferring an injectable material into the first housing through the orifice; and injecting the injectable material through the orifice.

Embodiments may contain one or more of the following features. Injecting the material comprises reacting a chemical pyrotechnic material. Transferring the material comprises engaging the first housing with a second housing configured to house the material. Transferring the material further comprises displacing a member in the second housing. Transferring the material further comprises engaging the second housing with a third housing.

In another aspect, the invention features a method of providing an injection device comprising: providing a first housing formed of a first material and configured to house an injectable material; providing a second housing defining an orifice, the second housing formed of a second material different than the first material, the first and second housings configured to mate together wherein the first housing is capable of transferring the injectable material to the second housing, the second housing having a propellant, e.g., a chemical propellant, configured to displace the injectable material through the orifice and out of the second housing; and mating the first and second housings together.

Embodiments may contain one or more of the following features. The method further comprises transferring the injectable material from the first housing to the second housing through the orifice. The method further comprises injecting the injectable material through the orifice.

In yet another aspect, the invention features a method of providing an injection device comprising: providing a first housing formed of a first material and configured to house an injectable material; providing a second housing defining an orifice, the second housing formed of a second material different than the first material, the first and second housings configured to mate together wherein the first housing is capable of transferring the injectable material to the second housing, the second housing having a propellant configured to displace the injectable material through the orifice and out of the second housing; and optionally providing instructions for using the injection device. In another embodiment, the method further comprises placing the injectable material in the first housing.

In another aspect, the invention features a method of providing a needleless injection device powered by a chemical propellant, e.g., a pyrotechnic material or a propellant that undergoes a chemical reaction to produce a gas. The method can include providing, e.g., manufacturing, a first housing as described herein; providing, e.g., manufacturing, a second housing as described herein; and optionally, combining the first and second housings or providing instructions to another entity to combine them.

In a preferred embodiment, one compound, e.g., a liquid, e.g., a diluent, is disposed in one housing, and a second compound, e.g., a dry compound, e.g., a lyophilized material, is disposed in another housing. In a preferred embodiment, both compounds are disposed in one housing.

In a preferred embodiment, a first entity places a first compound, e.g., a diluent, in one housing, and a second entity places a second compound, e.g., a lyophilized material, in another housing. In a preferred embodiment, one entity places a first compound in a first housing and places a second compound in a second housing.

In a preferred embodiment, one or both of the first and second entities provide instructions to a third entity, e.g., a healthcare provider or a patient, to combine the first and second housings.

As used herein, "injectable material" refers to any material or mixture of materials that can be injected into the body of a subject, e.g., a human or an animal. For example, an injectable material can be a fluid, e.g., a diluent or a diluent and a drug.

Other features, objects, and advantages of the invention will be apparent from the description and drawings, and from the claims.

DESCRIPTION OF DRAWINGS

FIG. 1 is a perspective view of an embodiment of an injection system.

FIG. 2 is a perspective view of an embodiment of an injector device.

FIG. 3 is a perspective view of an embodiment of a fluid transfer device.

FIG. 6 is an exploded perspective view of the fluid transfer device of FIG. 3.

FIG. 7 is an end view of the fluid transfer device of FIG. 3.

FIG. 8 is a cross sectional view of the fluid transfer device of FIG. 7, taken along line 8-8.

FIG. 9 is a cross sectional view of the fluid transfer device of FIG. 7, taken along line 9-9.

FIG. 10 is an exploded perspective view of an embodiment of an injector device.

FIG. 11 is an end view of the injector device of FIG. 10.

FIG. 12 is a cross sectional view of the injector device of FIG. 11, taken along line 12-12.

FIG. 13 is a cross sectional view of the injector device of FIG. 11, taken along line 13-13.

FIG. 14 is an end view of an embodiment of an injector device.

FIG. 15 is a cross sectional view of the injector device of FIG. 14, taken along line 15-15.

FIG. 16 is a cross sectional view of the injector device of FIG. 14, taken along line 16-16.

FIG. 17 is a perspective view of an embodiment of a charge cup.

FIG. 18 is an end view of an embodiment of an injector device.

FIG. 19 is a cross sectional view of the injector device of FIG. 18, taken along line 19-19.

FIG. 20 is a cross sectional view of the injector device of FIG. 18, taken along line 20-20.

FIG. 23 is an exploded perspective view of the injection system of FIG. 21.

FIG. 25 is an end view of an embodiment of an injector device.

FIG. 26 is a cross sectional view of the injector device of FIG. 25, taken along line 26-26.

FIG. 27 is a cross sectional view of the injector device of FIG. 25, taken along line 27-27.

FIG. 28 is a detailed view of the injector device of FIG. 26.

FIG. 29 is an exploded perspective view of the injector device of FIG. 26.

DETAILED DESCRIPTION OF THE PREFERRED EMBODIMENT

The invention relates to injection systems and devices that can be used in injection systems.

Figure 4:
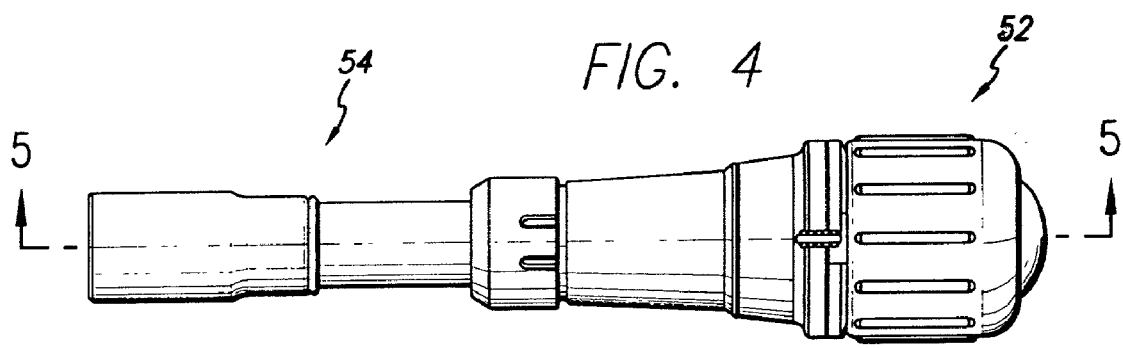
FIG. 4 is a side view of the injection system of FIG. 1.
Figure 5:
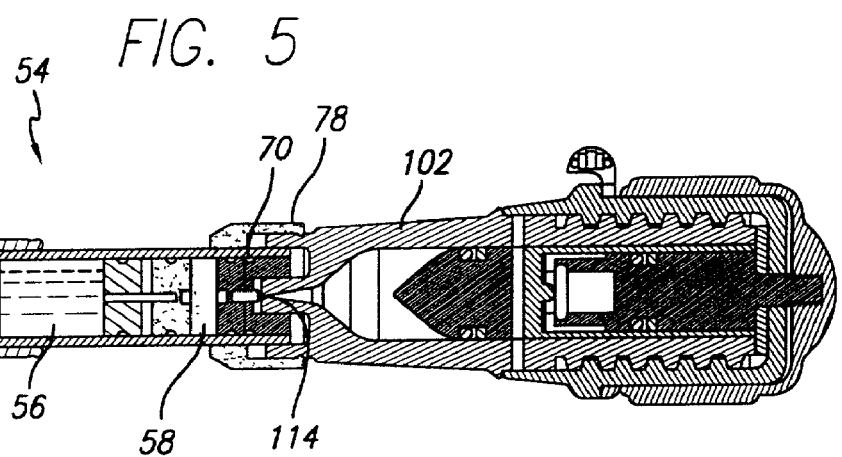
FIG. 5 is a cross sectional view of the injection system of FIG. 1.

Referring to FIGS. 1-5, a needleless injection system 50 includes an injector device 52 and a fluid transfer device 54. Injector device 52 and fluid transfer device 54 are configured to mate with each other (FIGS. 1, 4 and 5). Generally, fluid transfer device 54 contains an injectable fluid 56, such as an aqueous diluent, e.g., a saline solution, and another material 58, such as a lyophilized material, separate from the injectable fluid (FIG. 5). Injector device 52, which contains a multi-component charge system, is configured to receive injectable fluid 56 and material 58 from fluid transfer device 54, and to inject mixed fluid and material to a subject, e.g., a human.

Fluid transfer device 54 is generally configured to house one or more injectable materials, e.g., fluid 56 and material 58. Referring to FIGS. 6-9, device 54 includes a vial 60, here, a cylindrical tube made of a material that is stable and substantially inert to fluid 56 and material 58 for extended periods of time, e.g., over the shelf life of the injectable material. Typically, the material for vial 60 is relatively rigid and relatively impervious to diffusion and evaporation, such that, for example, fluid 56 does not leach out of the vial. Materials include, for example, those that are FDA-approved and/or those used for pharmacological purposes, such as glass, polymers, and metal-containing materials.

Typically, vial 60 contains therein four stoppers that define separate cavities for fluid 56 and material 58. Starting at its top or proximal end, vial 60 includes a top stopper 62, a first middle stopper 64, a second middle stopper 66, and a bottom stopper 68 located at the bottom or distal end of the vial. Top stopper 62 includes a centrally positioned top needle 70, e.g., a stainless steel or relatively hard plastic needle, and a pierceable portion 72 adjacent to the bottom or distal end of the top needle. At its top or proximal end, top needle 70 is configured to engage with an orifice of injector device 52 (described below). First and second middle stoppers 64 and 66 are connected together by a middle needle 74. At its distal end, middle needle 74 is secured to second middle stopper 66; and at its proximal end, the middle needle is adjacent to a pierceable portion 76 of first middle stopper 64. Bottom stopper 68 seals the distal end of vial 60 and is configured to engage with a pushrod (described below). Thus, referring particularly to FIGS. 8 and 9, top stopper 62 and first middle stopper 64 define a first cavity that houses material 58; and second middle stopper 66 and bottom stopper 68 define a separate second cavity that houses fluid 56.

In general, stoppers 62, 64, 66, and 68 can be made of any material that can provide a good seal, e.g., a liquid-tight and/or air-tight seal, with vial 60. As an example, a suitable stopper material is a resilient material such as butylene rubber. Typically, the stoppers should be movable within vial 60 while still providing a good seal with the vial. In embodiments, stoppers 62, 64, 66, and 68 can be made of the same material or different materials.

Fluid transfer device 54 further includes an adaptor 78 and a base 80. Adaptor 78 is configured to receive and to secure the proximal end of vial 60 so that fluid transfer device 54 can engage with injector device 52. Adaptor 78 can include one or more tangs 82 that enhance connection to and release from injector device 52. Base 80 is configured to receive the distal or bottom end of vial 60. Base 80 includes an integrally formed pushrod 84 that can engage with bottom stopper 68 during use (described below).

Other embodiments of fluid transfer devices are possible and are described in U.S. Provisional Patent Application Ser. Nos. 60/250,410; 60/250,425; 60/250,537; and 60/250,573, all filed on Nov. 30, 2000, and all entitled "Injection Devices", the entire contents of which are all hereby incorporated by reference. For example, in embodiments, a fluid transfer device may include only two stoppers that define a cavity for a fluid only, as described in U.S. Ser. No. 60/250,573. In embodiments, a fluid transfer device may include a material housed in a stopper and sealed in a powder pack, as described in U.S. Ser. No. 60/250,410. Combinations of such embodiments can be used.

Injector device 52 is generally configured to receive injectable material (fluid 56 and material 58) transferred from fluid transfer device 54 and to deliver the material to a subject. As described below, numerous embodiments of injector device 52 are possible.

Referring to FIGS. 10-13, in some embodiments, an injector device 100 includes a multi-component charge that is activated electrically, here, with a two-lead design. Injector device 100 generally includes, starting distally, an injector 102, an injector cap 104, and a battery cap 106 located proximally. Injector 102, injector cap 104, and battery cap 106 are attached coaxially by threaded connections 108 and 110. Injector 102 defines a chamber 112, here, a generally elongated cylindrical cavity, that receives injectable material, and an orifice 114 (in fluid communication with chamber 112) through which the injectable material is delivered to the chamber and expelled during use. Orifice 114 is generally configured for needleless injection. Injector 102 is generally made of a material that is more break-resistant than the material of vial 60. Preferably, the material of injector 102 is resistant to mechanical shock from discharge of the charge, e.g., the injector material has a burst strength greater than the pressure generated by the charge (as described below). The material of injector 102 preferably fails non-catastrophically, e.g., does not shatter, if exposed to sufficient mechanical shock. Suitable materials for injector 102 include, for example, polycarbonates and polysulfones.

Inside injector 102 and injector cap 104, device 100 includes a piston 116, a charge sleeve 118, and a charge cup 120. In general, during use, piston 116 and charge sleeve 118 are slidably movable within injector 102, while charge cup 120 is fixedly secured between the injector and injector cap 104 (FIGS. 12 and 13). Piston 116 includes an O-ring 122 and a backup ring 124 that provide a tight, but movable, seal between the piston and the wall of chamber 112. Similarly, charge cup 120 includes an O-ring 126 and a backup ring 128 that provide a tight seal between the charge cup and charge sleeve 118, while still allowing the charge sleeve to slide within injector 102. Charge cup 120 further defines a charge cavity 130 in which the charge is placed. After the charge is loaded in cavity 130, the charge is covered and sealed with a burst membrane 132 and covered with a nozzle 134. Burst membrane 132 can be, for example, a 0.005 inch thick disc of Mylar® foil. Nozzle 134, which fits over a portion of charge cup 120, is a cylindrical cup having an opening at its base. Nozzle 134 provides a good interference fit between charge cup 120 and charge sleeve 118, and can also minimize any bulging of the charge cup near cavity 130 due to packing of the charge in the cavity. Piston 116 and charge cup 120 can be made of, e.g., injection molded polymer such as polycarbonate. Nozzle 134 and charge sleeve 118 can be made of, e.g., stainless steel.

In some embodiments, the charge includes a mixture of a propellant (e.g., 1:1 copper oxide and 5-aminotetrazole, or 5AT) and a triggering material (e.g., sucrose and potassium chlorate). Numerous other systems can be used. Generally, specific compositions for charge systems are determined empirically, taking into account, for example, the size of the injector, the amount of injectable material to be delivered, and the size of the orifice. A non-limiting, illustrative list of examples of chemical components that can be used are disclosed in U.S. Pat. Nos. 4,103,684; 4,342,310; 4,447,225; 4,518,385; 4,592,742; 4,623,332; 4,680,027; 4,722,728; 4,913,699; 5,024,656; 5,049,125; 5,064,123; 5,190,523; 5,304,128; 5,312,335; 5,334,144; 5,383,851; 5,399,163; 5,499,972; 5,501,666; 5,503,628; 5,520,639; 5,569,189; 5,630,796; 5,704,911; 5,730,723; 5,840,061; 5,851,198; 5,879,327; 5,899,879; 5,899,880; 5,911,703 and 5,993,412, each of which is hereby incorporated by reference.

As mentioned above, injector device 100 electrically activates or ignites the charge. Charge cup 120 further includes two wire leads 136 connectable to an electrical energy source. Leads 136 extend from cavity 130 (and the charge) to an energy source, here, a battery 138. Battery 138, e.g., a lithium coin battery, is secured between injector cap 104 and battery cap 106. Battery 138 is nested in an electrically-conducting contact can 140 along with a cushion disc 142 made of a resilient material. Contact can 140 has a rim configured to contact one terminal of battery 138, and an opening 144 that allows one of leads 136 to contact another terminal of the battery. Cushion disc 142 can minimize recoil during use of injector device 100 and allows battery 138 to be depressed to contact one of the leads 136 (described below).

Turning now to leads 136, at their distal ends, the leads terminate near charge cavity 130. Leads 136 can terminate anywhere along the longitudinal length of cavity 130, depending on which part of the charge is to be exposed to activation or ignition. The distal ends or portions of leads 136 are electrically connected together, e.g., by a tungsten filament (not shown) that extends across cavity 130, e.g., transverse to the longitudinal length of the cavity. In some embodiments, the surface of cavity 130 can be coated with an electrically-conducting layer, and the distal portions of leads 136 can be electrically connected together via the electrically-conducting layer. At their proximal ends, one of leads 136 contacts contact can 140, and the other one of the leads extends through opening 144 and is slightly spaced from a terminal of battery 138 (FIG. 12).

In operation, injectable material, i.e., fluid 56 and material 58, is transferred from fluid transfer system 54 to injector device 100; the system and the device are separated; and the injectable material is ejected from the injector device. Referring again to FIG. 5, injector 102 and adaptor 78 are connected together, e.g., snap fit together. Orifice 114 and top needle 70 are engaged in fluid communication with each other.

With fluid transfer device 54 and injector device 100 connected, the injector device is pushed down or distally, with base 80 stationary, e.g., against a fixed, flat surface. As pressure develops in vial 60 to a sufficient or predetermined level, top needle 70 pierces pierceable portion 72, and middle needle 74 pierces pierceable portion 76. As injector device 100 is pushed down, pushrod 84 advances bottom stopper 68 up. As injector device 100 is continued to be pushed down, fluid 56 is transferred through middle needle 74 to the cavity between top stopper 62 and first middle stopper 64 where the fluid mixes with material 58. The mixed material is transferred through top needle 70, through orifice 114, and into chamber 112. Injector device 100 is advanced down until a predetermined amount of fluid 56, material 58, and/or mixed material are transferred to the injector device, at which time the injector device is disconnected from fluid transfer device 54.

To inject the mixed material from injector device 100, orifice 114 is placed adjacent to a predetermined injection site, and battery 138 is pushed distally or down. As battery 138 is pushed down, one of its terminals contacts the spaced proximal end of one of the leads 136 (FIG. 12), thereby completing an electrical loop between the leads 136 (since the other lead is already connected to the other terminal of the battery via contact can 140). Electrical energy from battery 138 flows through the filament extending across the charge, and ignites the charge. The activated or ignited charge generates gas, i.e., pressure, in cavity 130. The gas ruptures burst membrane 132 at a predetermined pressure and propels charge sleeve 188 and piston 116 distally, thereby pushing the injectable material through orifice 114 and into the injection site.

FIGS. 14-16 show another embodiment of an injector device 150, in which elements similar to elements described above are designated with the same reference characters. Injector device 150 includes a separate cup 152 for housing the charge and a modified arrangement of wire leads. Cup 152 further minimizes any bulging of charge cup 120 due to packing of the charge. Cup 152 allows the charge to be prepared separately from charge cup 120. Cup 152 also allows the charge to be prepared modularly, e.g., like tailorable bullet modules that can be loaded into predetermined injector devices according to medication, dosage, delivery rate, etc.

Referring particularly to FIG. 17, cup 152 includes two slots 154 and two grooves 156. Slots 154 are configured to receive a wire or a filament (not shown) that extends across the longitudinal length of cup 152 and through the charge. The wire, e.g., a tungsten filament, can be secured to cup 152 with an electrically-conducting material, such as an electrically-conducting epoxy. Slots 154 are also designed so that the wire or filament can be relatively easily threaded and attached to cup 152. Grooves 156 extend along the side of cup 152 and to the bottom of the cup (FIG. 15). Grooves 156 and the top surface or rim 160 of cup 152 are coated with an electrically-conducting layer, e.g., a metal layer, such that the layer can electrically contact the wire or filament. Thus, electrically-conducting material in one of the grooves 156 at the bottom of cup 152 is in electrical communication with electrically-conducting material in another one of the grooves at the bottom of the cup via the grooves on the side of the cup, rim 160, and the wire or filament. In other embodiments, cup 152 can have more than two slots 154 and/or grooves 156 that can be arranged in different arrangements, e.g., asymmetrically arranged around the cup.

Referring particularly to FIG. 15, injector device 150 further includes two wire leads 158. At their distal ends, one of the leads 158 electrically contacts electrically-conducting material formed in one of the grooves 156 at the bottom of cup 152, and the other lead contacts electrically-conducting material formed in the other groove 156 at the bottom of the cup. At their proximal ends, one of the leads 158 contacts contact can 140, and the other lead is spaced from battery 138, as described above. In use, injectable material is transferred to injector device 150 and ejected from the device as generally described above.

FIGS. 18-20 show another embodiment of an injector device 170, in which elements similar to elements described above are designated with the same reference characters. Injector device 170 is generally similar to injector device 100, but modified to include one center lead 172 instead of two leads 136. At its proximal end, lead 172 contacts a terminal of a battery assembly 174, here, two lithium coin batteries. At its distal end, lead 172 extends through cavity 130, and a distal portion of the lead is crimped to an electrically-conducting filament 176 by an electrically-conducting tube 178. Filament 176 extends through the charge in cavity 130, between burst membrane 132 and the distal end of charge cup 120, and between the charge cup and nozzle 134 where the filament contacts a contact strip 180. Contact strip 180 also contacts charge sleeve 118. Electrical contact is continued from contact strip 180 to a second contact strip 182, for example, by making charge sleeve 118 out of an electrically-conducting material such as stainless steel or by connecting the contact strips with a filament. Second contact strip 182 is capable of contacting a second terminal of battery assembly 174. For example, second contact strip 182 can be connected to contact can 140, e.g., by a filament, and the contact can may have a portion that is spaced from, but capable of contacting, the second terminal of battery assembly 174. The portion can be contacted with the second terminal, e.g., by depressing a button 184 and cushion disk 142. Device 170 can be triggered by depressing button 184, which completes an electrical loop to ignite the charge.

FIGS. 21, 22A, 22B, and 23 show another embodiment of an injection system 200 wherein a fluid transfer device is integrated with an injector device. Elements similar to elements described above are designated with the same reference characters. System 200 includes an injector 202, an injector cap 204, and a removable safety band 206. Injector 202 defines a chamber 210 and an orifice 212, as generally described above. In some embodiments, chamber 210 contains an injectable material, such as a lyophilized material. In some embodiments, chamber 210 is empty. Injector 202 and injector cap 204 are movable relative to one another by a threaded connection 208 when safety band 206 is removed from system 200, e.g., by a user.

Within injector 202 and injector cap 204, system 200 includes a piston 214, a vial 216, and a charge cup 218. Piston 214 includes an O-ring 220 and a backup ring 222, as generally described above. Piston 214 defines a lumen 224 that extends transverse to the length of the piston, and an annular tab 225. Tab 225 engages a portion of injector 202 to keep piston 214 stationary when fluid is transferred through the piston (described below). Tab 225 is also configured to separate, e.g., shear, from piston 214 under a predetermined force, e.g., a force of injection. Disposed within piston 214 is a piercing element 226, e.g., a hollow needle, that is in fluid communication with lumen 224 and extends proximally where it engages a stopper seal 227. Stopper seal 227 seals the proximal end of piercing element 226. For example, in embodiments in which chamber 210 contains a material, such as a sprayed dried or lyophilized powder, stopper seal 227 can be used with piston 214 to seal the chamber to protect the material from exposure, e.g., to air. Orifice 212 can be sealed with a removable barrier. Vial 216, e.g., a glass vial as described above, is coaxially positioned within injector 202.

Within vial 216 are a distal stopper 228 and a proximal stopper 230 that contain an injectable fluid 232 therebetween. Distal stopper 228, e.g., made of a biocompatible or inert material, such a butyl rubber, includes a pierceable portion 234 adjacent to stopper seal 227. Proximal stopper 230 includes an outer portion 229 and an inner core 231. In some embodiments, outer portion 229 and inner core 231 are formed of different materials. For example, outer portion 229 can be formed of a material, e.g., a butyl rubber, that is relatively inert to fluid 232 and provides a tight seal with vial 216; and core 231 can be formed of a relatively rigid material having a relatively high durometer. Core 231 can provide system 200 with predictable injections, e.g., by minimizing undesirable harmonics during injection. Charge head 218, including embodiments for igniting the charge, can be any of the embodiments described above and below, for example, as in injector device 100, 150, or 170.

Figure 24A:
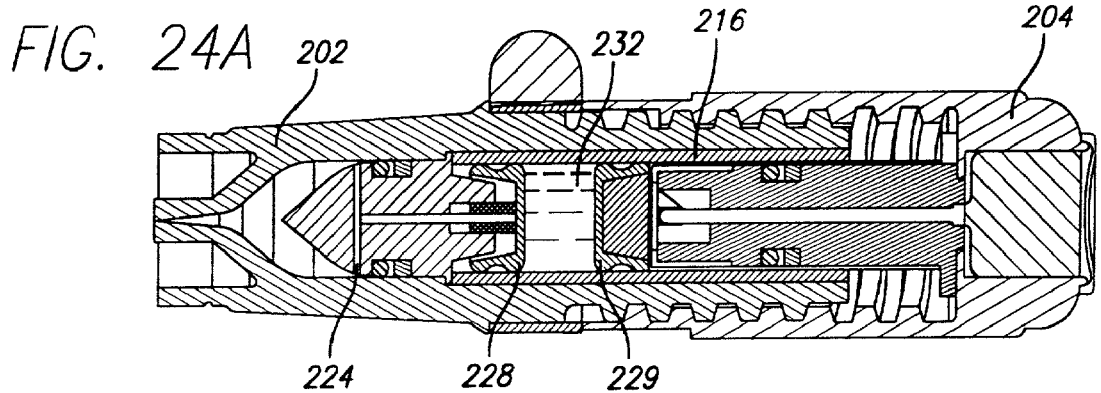
FIGS. 24A, 24B, 24C, and 24D are cross sectional views of the injector system of FIG. 21 during use.
Figure 24B:
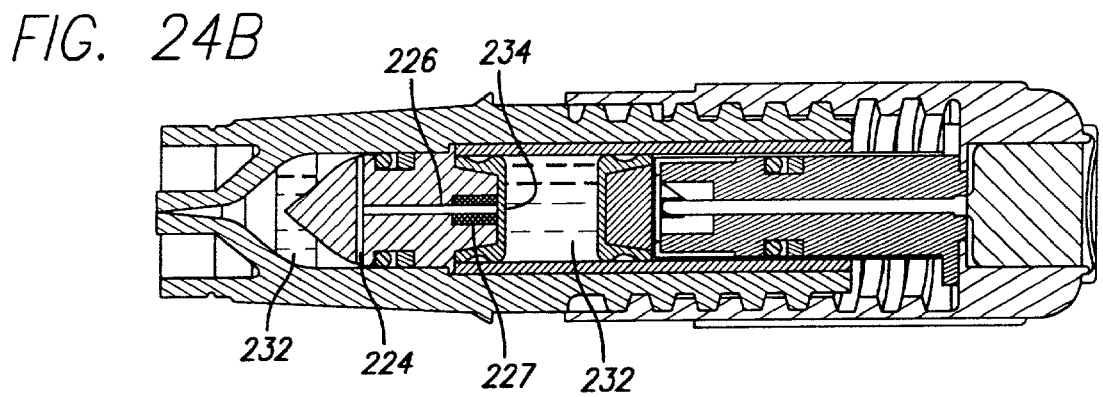
Figure 24C:
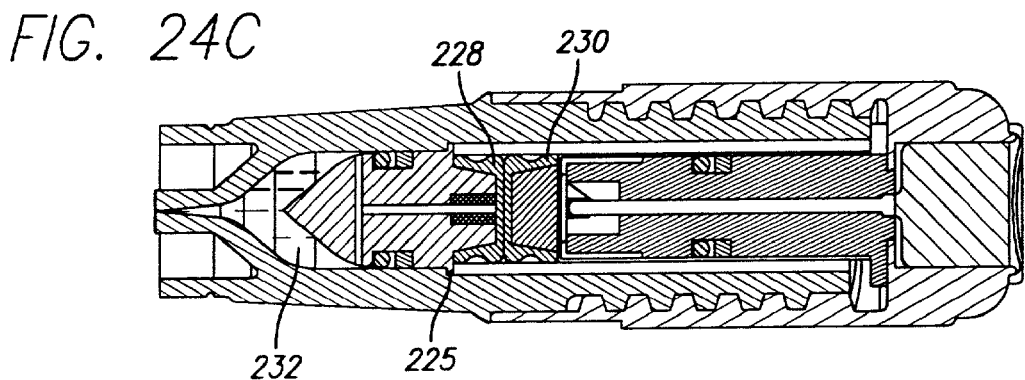
Figure 24D:
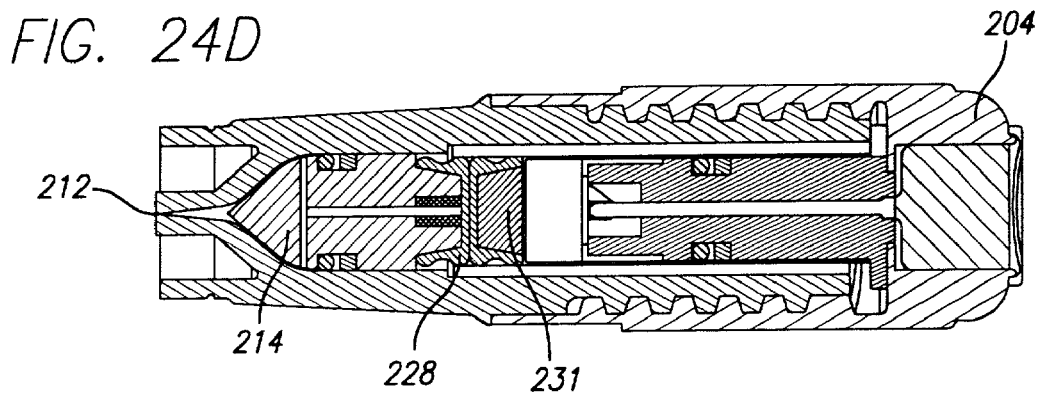

FIGS. 24A-24D show one embodiment of a method of using injection system 200. Safety band 206 is removed to allow injector cap 204 to be rotated to advance the injector cap toward orifice 212, i.e., distally. As injector cap 204 advances distally, distal and proximal stoppers 228 and 230 are also forced distally such that piercing element 226 pierces stopper seal 227 and portion 234 of the distal stopper (FIG. 24B). Tab 225 keeps piston 214 generally stationary. As the injector cap is advanced further, fluid 232 is transferred from between stoppers 228 and 230, through piercing element 226, through lumen 224, and into chamber 210, where, in some embodiments, the fluid mixes with another material, e.g., a lyophilized material. Injector cap 204 is advanced distally until all of fluid 232 is transferred into chamber 210 (FIG. 24C). Distal stopper 228 mates with piston 214. Injectable material, i.e., fluid 232 or fluid mixed with another material, is expelled through orifice 212 by triggering charge head 218 as described above. Triggering the charge head propels the charge sleeve distally, which propels stoppers 228 and 230 and piston 214 distally (and shears tab 225), thereby expelling the injectable material through orifice 212 (FIG. 24D).

In some embodiments, proximal stopper 230 can be made of one material, e.g., integrally formed of one material. Distal stopper 288 can be formed of multiple materials, as described above for stopper 230. In certain embodiments, e.g., in which only a fluid is injected, e.g., no lyophilized material, stopper seal 227 and distal stopper 228 can be integrally formed as one component. In such embodiments, stopper seal 227 and stopper 228 can be formed of the same or different materials. In embodiments, piston 214 and piercing element 226 can be integrally formed. For example, piston 214 can define a proximal piercing portion capable of piercing stopper seal 227 and distal stopper 228. The proximal piercing portion is capable of establishing fluid communication between lumen 224 and material 232. Other configurations of lumen 224 are possible to transfer material 232 from one end of piston 214 to another end.

FIGS. 25-29 show another embodiment of an injector device 250 in which the charge is ignited non-electrically, here, chemically. Device 250 includes an injector 252, an injector cap 254 connected to the injector by a threaded connection 258, and a safety cap 256. Injector 252 defines an orifice 260 and a chamber 262 for injectable material, generally as described above.

Within injector 252 and injector cap 254, device 250 includes a piston 264 and a charge cup 266. Piston 264 includes a piston O-ring 268 and a piston backup ring 270; and charge cup 266 includes a charge cup O-ring 272 and a backup ring 274, as generally described above. Charge cup 266 defines a charge cavity 282, a breakable capsule 284, and a burst membrane 286. As described below, charge cavity 282 contains a charge, and capsule 284 contains a material capable of activating or igniting the charge, e.g., a catalyst or an oxidizing agent such as sulfuric acid.

Proximal of piston 264, device 250 further includes a shear pin 276, a movable charge sleeve 278, and a nozzle 280. Shear pin 276 holds charge sleeve 278 stationary at an initial position until a predetermined pressure is generated by the charge. Charge sleeve 278 includes a projection 288 that abuts against burst membrane 286 and capsule 284 (FIG. 28). Device 250 also includes a gasket 294 that, during use, minimizes recoil and allows safety cap 256 to be advanced distally (described below).

Safety cap 256 includes a removable safety tab 292, e.g., a strip of plastic. Safety cap 256 is attached to device 250 by a threaded connection 290 defined by the proximal end of charge cup 266.

In operation, device 250 is fired by removing safety tab 292 from the device, which allows safety cap 256 to be pushed distally, toward orifice 260, which is abutted against a surface, e.g., a subject's skin. As safety cap 256 is pushed distally (by a distance approximately equal to the thickness of safety tab 292 via threaded connection 290), projection 288 deforms burst membrane 286 and breaks capsule 284, thereby releasing the activating or igniting material inside the capsule. The activating material reacts with the charge in cavity 282 and generates pressure. The pressure increases inside cavity 282 until burst membrane 286 ruptures and the force against charge sleeve 278 is sufficient to break shear pin 276. This pressure moves sleeve 278 distally, thereby pushing piston 264 distally and expelling injectable material in chamber 262 through orifice 260.

FIGS. 34-38 show another embodiment of an injection system 350 including an injector device 352 and a power unit 354. Injector device 352 can be disposable, and power unit 354 can be reusable.

Figure 35:
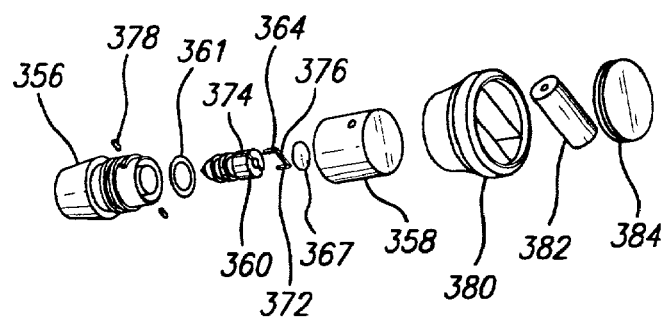
FIG. 35 is an exploded perspective view of the injector system of FIG. 34.
Figure 36:
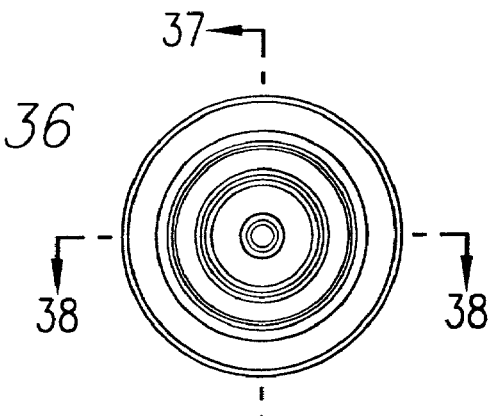
FIG. 36 is an end view of the injector system of FIG. 34
Figure 37:
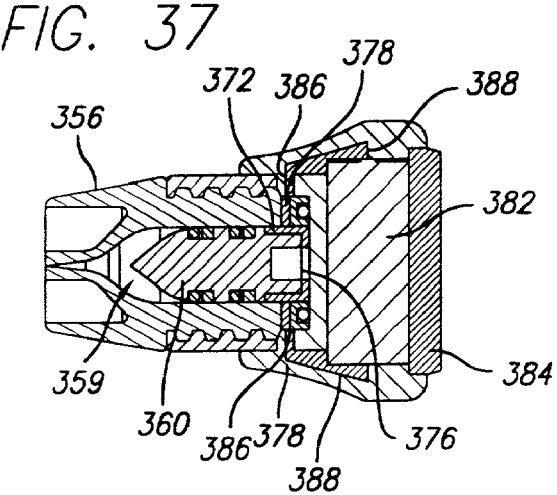
FIG. 37 is a cross sectional view of the injector system of FIG. 36, taken along line 37-37.
Figure 38:
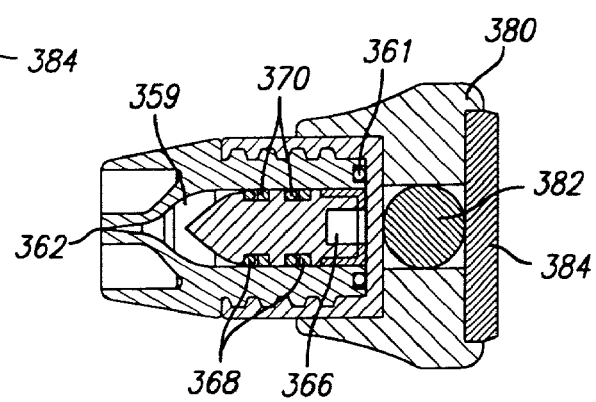
FIG. 38 is a cross sectional view of the injector system of FIG. 36, taken along line 38-38.

Referring particularly to FIG. 35, injector device 352 includes an injector 356 and an injector cap 358 connectable to the injector by a threaded connection and sealable with a face seal 361, e.g., an O-ring. Injector 356 defines a cavity 359 and an orifice 362, as generally described above. Within injector 356 and cap 358, injector device 352 includes a piston 360, an electrically-conductive bridge 364 that engages the proximal end of the piston, and a membrane 367, e.g., a disc of paper, between the piston and injector cap 358. Piston 360 includes O-rings 368 and backup rings 370, and defines a charge cavity 366 at the proximal end, as generally described herein. That is, charge cavity 366 is integrally formed with piston 360. Bridge 364 includes two conductive members 372 that fit into two grooves 374 defined by piston 360. A wire 376, e.g., a tungsten filament, extends from one member 372, through a charge in cavity 366, and to the other member 372. Injector device 352 further includes two electrically-conductive leads 378 that extend from members 372 and through injector 356 to contact power unit 354.

Figure 34:
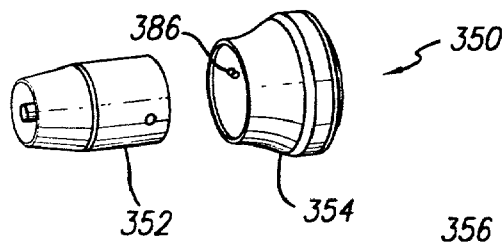
FIG. 34 is a perspective view of an embodiment of an injection system.

Power unit 354 includes an adaptor 380, a battery 382, and a switch 384. Adaptor 380 is configured to connect to injector device 352 and to trigger the injector device. Numerous embodiments are possible. In some embodiments, adaptor 380 includes two extensions 386 that engage with injector device 352 (FIG. 34). Each extension 386 has a conductive lead 388 therein that extends from lead 378 to battery 382, where the leads are capable of contacting a terminal of the battery. Switch 384 is configured to selectably connect the terminals of battery 382 to leads 388, thereby passing a current through the leads. For example, a spring can be placed between injector cap 358 and battery 382 to push battery proximally, and by depressing switch 384 distally, the terminals of the battery can be urged distally into contact with leads 388. Other embodiments of switch 384 are possible.

In operation, an injectable material (not shown) is placed cavity 359, and orifice 362 is placed adjacent to an injection site. Switch 384 is then activated such that an electrical current flows from battery 382 and through leads 388, leads 378, members 372, and filament 376. The current flowing through filament 376 ignites the charge in cavity 366. The ignited charge generates pressure as described herein and propels piston 360 distally, thereby ejecting the injectable material out of cavity 359, through orifice 362, and into the injection site. After injection, injection device 352 can be disconnected from power unit 354, and another injection device can be connected to the power unit.

Other embodiments of injector devices are possible and are described in incorporated-by-reference U.S. Provisional Patent Application Ser. Nos. 60/250,410; 60/250,425; 60/250,537; and 60/250,573.

The injectable material can include one or more substances. For example, the second substance can be a liquid, e.g., a diluent or solute. Such liquids can include buffers, inert fillers, pharmaceutically acceptable carriers, or the like.

The substance can be a dry substance, e.g., a lyophilized protein, nucleic acid, e.g., RNA or DNA, or polysaccharide. The substance can be a vaccine, or a drug. The substance can be a peptide, polypeptide, or protein, e.g., an antibody, an enzyme, a hormone or growth factor. Preferred substances include insulin. The substance can be: a blood protein, e.g., clotting factor VIII or a IX, complement factor or component; a hormone, e.g., insulin, growth hormone, thyroid hormone, a catecholamine, a gonadotrophin, PMSG, a trophic hormone, prolactin, oxytocin, dopamine and the like; a growth factor, e.g., EGF, PDGF, NGF, IGF's and the like; a cytokine, e.g., an, interleukin, CSF, GMCSF, TNF, TGF-alpha, TGF-beta. and the 25 like; an enzyme, e.g., tissue plasminogen activator, streptokinase, cholesterol biosynthetic or degradative, glycosolases, and the like; a binding protein, e.g., a steroid binding protein, a growth hormone or growth factor binding protein and the like; an immune system protein, e.g., an antibody, SLA or MHC gene or gene product; an antigen, e.g., a bacterial, parasitic, or viral, substance or generally allergens and the like. The substances can be combined by the subject, or by another person.

The subject can be a human or an animal, e.g., a laboratory animal, or pet, e.g., a dog or cat, or other animal, e.g., a bovine, a swine, a goat, or a horse.

Therapeutic agents that can be used in the devices and methods described herein include, for example, vaccines, chemotherapy agents, pain relief agents, dialysis-related agents, blood thinning agents, and compounds (e.g., monoclonal compounds) that can be targeted to carry compounds that can kill cancer cells. Examples of such agents include, insulin, heparin, morphine, interferon, EPO, vaccines towards tumors, and vaccines towards infectious diseases.

The device can be used to deliver a therapeutic agent to any primate, including human and non-human primates. The device can be used to deliver an agent, e.g., a therapeutic agent to an animal, e.g., a farm animal (such as a horse, cow, sheep, goat, or pig), to a laboratory animal (such as a mouse, rat, guinea pig or other rodent), or to a domesticated animal (such as a dog or cat). The animal to which the therapeutic agent is being delivered can have any ailment (e.g., cancer or diabetes). It is expected that the device may be most useful in treating chronic conditions. However, the device can also be used to deliver a therapeutic agent (such as a vaccine) to an animal that is not suffering from an ailment (or that is suffering from an ailment unrelated to that associated with the therapeutic agent). That is, the device can be used to deliver therapeutic agents prophylactically.

The devices and methods of the invention can be used to individually tailor the dosage of a therapeutic agent to a patient.

The devices and methods of the invention can allow for outpatient treatment with increased convenience, such as, for example, without the use of an I.V.

Devices and methods described herein can be advantageous because they can be used to promote maintenance of the concentration of a therapeutic agent in a patient's plasma within a safe and effective range. Moreover, the device can release therapeutic agents in response to the concentration of an analyte in the patient's system. Thus, the rate of drug delivery can be appropriate for the patient's physiological state as it changes, e.g., from moment to moment.

The Charge

In general, the charge is formed of at least two discrete materials (e.g., at least two discrete materials, at least three discrete materials, at least four discrete materials, at least five discrete materials, at least six discrete materials, at least seven discrete materials, at least eight discrete materials, at least nine discrete materials, at least 10 discrete materials, at least 11 discrete materials, at least 12 discrete materials, at least 13 discrete materials, at least 14 discrete materials, at least 15 discrete materials, at least 16 discrete materials, at least 17 discrete materials, at least 18 discrete materials, at least 19 discrete materials, at least 20 discrete materials) formed as separate components. The discrete materials are typically used in combination to provide a desired pressure profile of the injectable fluid ejected by an injection device. Each discrete material can be formed of a single material or a combination of materials. In embodiments, by combining the discrete materials in a predetermined assembly or sequence, with a predetermined macroscopic shape(s), and/or with a predetermined microscopic structure(s), such as spheres or rods, the charge can propel, e.g., a piston with a predetermined pressure profile, i.e., pressure as a function of time. Accordingly, the piston can inject the injectable material from an injector with the predetermined pressure profile capable of injecting the injectable material effectively.

In general, the types of discrete materials used in a charge can include, for example, one or more triggers (a discrete material capable of generating relatively large amounts of gas and heat), one or more propellants (a relatively slow burning material) and/or one or more passive decay materials (a low-yielding material that continues the burn of the charge but which does not add a substantial amount of heat or kinetic effect).

In general, the order of the discrete material used in a charge can be varied as desired. As an example, a charge can have one or more propellants disposed between one or more triggers and one or more passive decay materials. As another example, a charge can have one or more triggers disposed between one or more propellants and one or more passive decay materials. As another example, a charge can have one or more passive decay materials disposed between one or more triggers and one or more propellants. As a further example, one or more propellants can be intercalated with one or more triggers and/or one or more passive decay materials. Combinations of these exemplary embodiments can be used. For example, in certain embodiments, a charge includes two or more discrete pyrotechnic materials that can react and deflagrate. Each pyrotechnic material can be formed of a single material or a combination of materials. Deflagrations can proceed at any desired rate (e g., several inches per second, several hundred feet per second). Examples of reactions that undergo deflagrations include those used in air bag chemistry and rocket motor chemistry.

Figure 30:
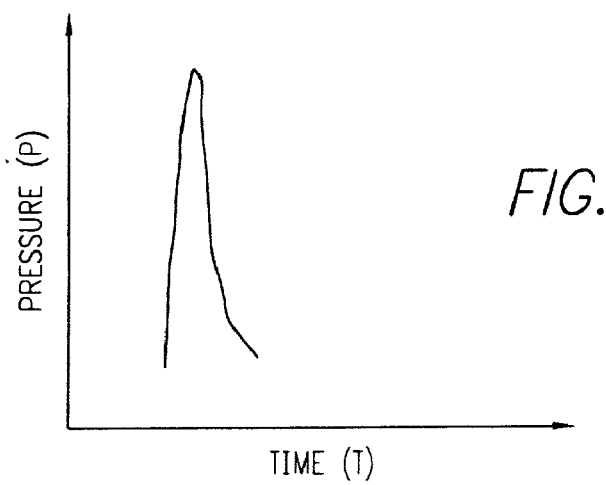
FIG. 30 is an illustrated plot of pressure as a function of time for a relatively fast burning material.
Figure 31:
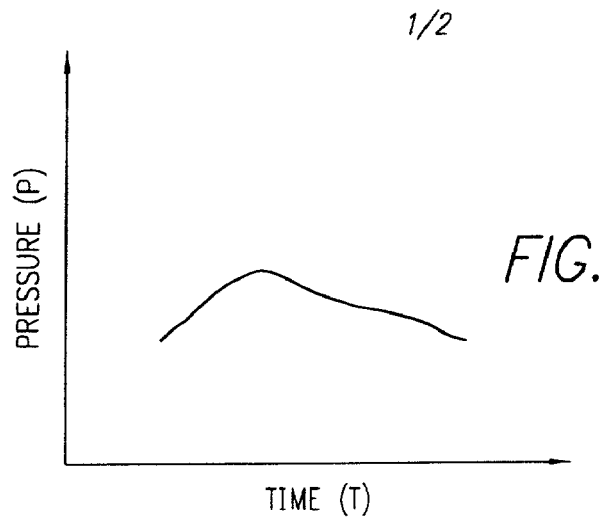
FIG. 31 is an illustrated plot of pressure as a function of time for a relatively slow burning material.

Typically, the charge is designed so that it is capable of generating pressure such that the injectable material can be ejected by an injection device with sufficient force to create an opening in the body (e.g., an opening in the skin of the body) through which the injectable material can be injected (FIG. 30). The opening can created, for example, relatively quickly and acceptably small to minimize pain and discomfort to the body. For example, in certain embodiments, the trigger can be capable of generating a relatively high initial pressure, such as about 4,000 psi, in a relatively short amount of time, such as about 1-5 msec, e.g., 1-2.5 msec. In some embodiments, the pressure profile of the trigger can have duration or latency of, for example, about 15 msec, with a final pressure of about 500 psi. In embodiments, the charge can be capable of generating sufficient pressure such that the injectable material can continue to keep the opening open so that the injectable material can be delivered through the opening at a desired dose, for a desired period of time and/or to a desired depth (e.g., cutaneous, subcutaneous, intramuscular, etc.) (FIG. 31). In embodiments, the charge can generate relatively large amounts of gas but relatively low amounts of heat. Preferably, the pressure generated by the charge does not enlarge the opening that can cause discomfort, and/or allow the opening to decrease in size, which can decrease the effectiveness of the injection by allowing the injectable material to leak back out of the opening. As an example, in some embodiments, the charge is capable of generating a relatively low initial and final pressures, such as about 700-800 psi and 200-300 psi, respectively. However, the latency of the pressure profile of the charge can be relatively large, such as about 500 msec.

Figure 32:
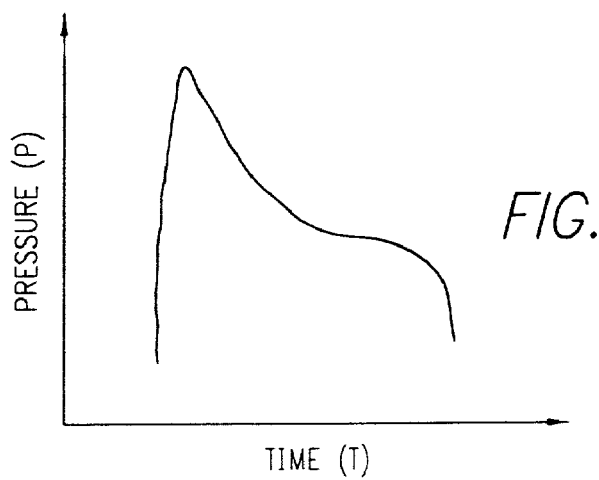
FIG. 32 is an illustrated plot of pressure as a function of time for a combination of relatively fast and slow burning materials.

By combining or loading the trigger, the propellant, and/or the passive decay material in a controlled manner in a charge cup or cavity, the charge can generate a pressure profile that is a combination of the pressure profiles of the trigger, the propellant, and/or the passive decay material, and which can effectively deliver the injectable material (FIG. 32).

Figure 33:
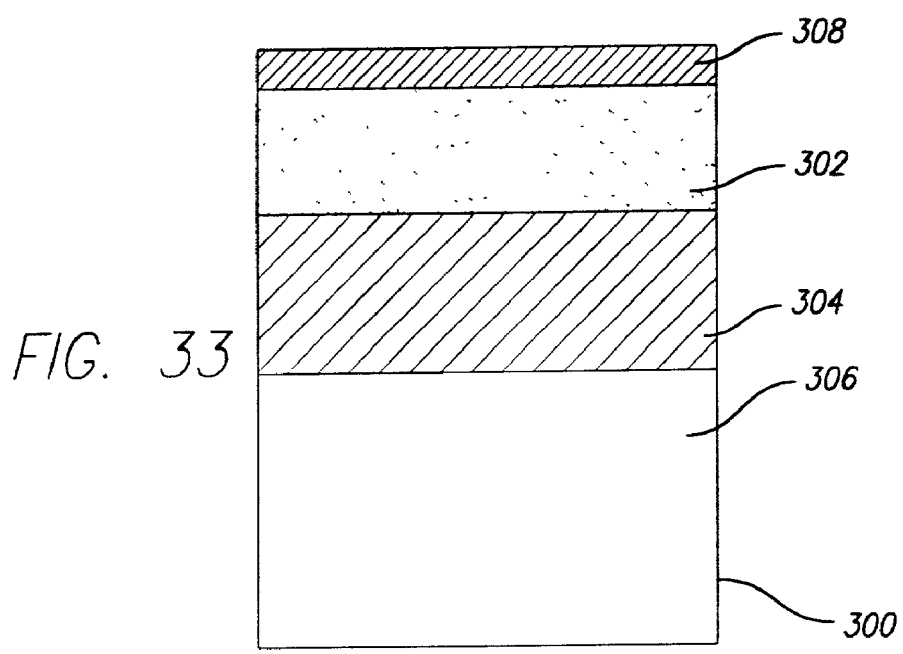
FIG. 33 is a schematic cross sectional view of an embodiment of a loaded charge cup.
Figure 21:
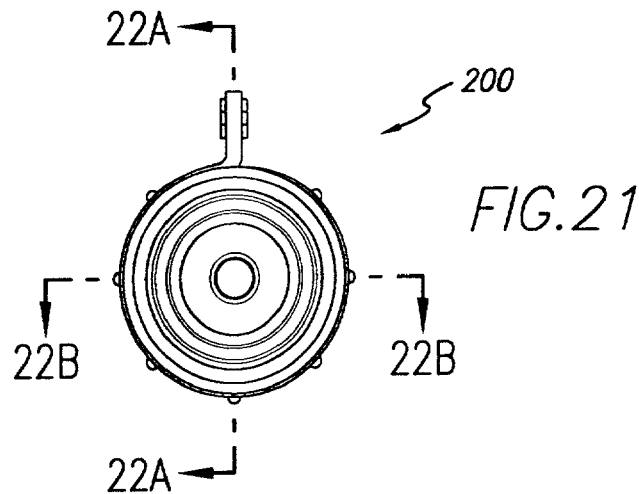
FIG. 21 is an end view of an embodiment of an injection system.
Figure 22A:
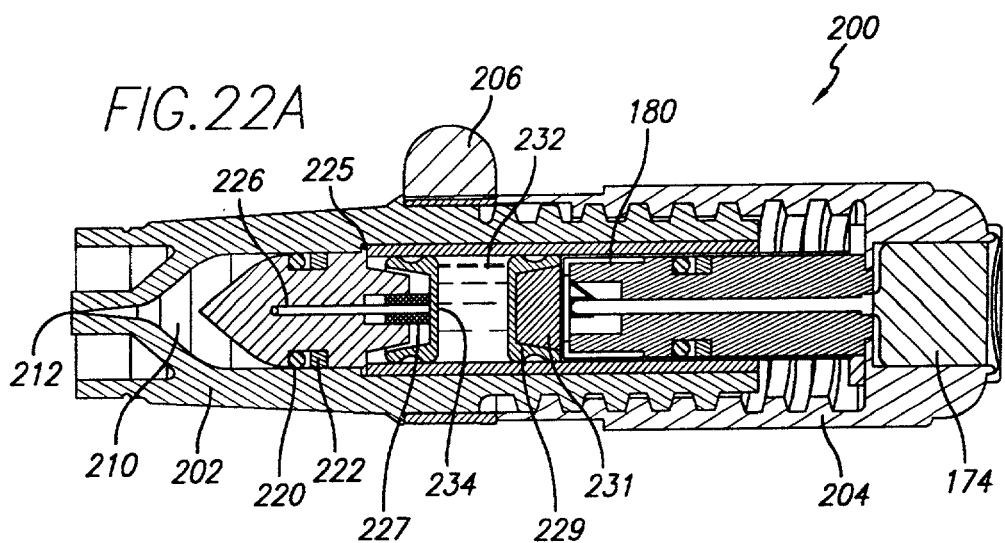
FIG. 22A is a schematic cross sectional view of the injection system of FIG. 21, taken along line 22A-22A.
Figure 22B:
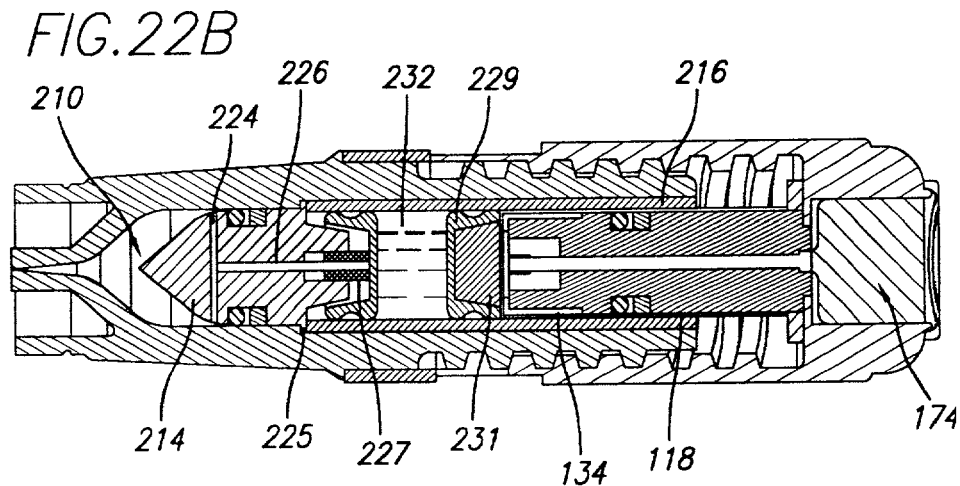
FIG. 22B is a schematic cross sectional view of the injection system of FIG. 21, taken along line 22B-22B.

FIG. 33 shows an example of a charge having three components loaded in a charge cup or cavity 300. Starting at a distal end, the charge has an igniter 302 (e.g., 75 mg of $BKNO_3$), a passive decay material 304 (e.g., 60 mg of gum arabic), and a propellant 306 (e.g., 120 mg of CuO/5 aminotetrazole). The sequence of the pyrotechnic materials can be adjusted according to the pressure profile desired, e.g., igniter/propellant/igniter. Similarly, the quantities of the pyrotechnic materials can be adjusted. At a distal end, charge cup 300 has a burst membrane 308 that acts a pressure dam so that a predetermined pressure can build up in the charge cup before the membrane ruptures and pressure is released to propel, e.g., the charge sleeve and piston. In other embodiments, the membrane can be replaced with, for example, a shear pin.

In operation, a user can trigger the charge by passing a current through a filaments, which can extend through the igniter. Triggering the charge causes the igniter to burn first, followed by the decay material, and then the propellant. Thus, the charge is capable of providing a multi-stage reaction that can deliver the injectable material with a desired pressure profile.

The desired pressure profile can also be controlled by tuning or shaping the charge and/or the pyrotechnic materials. For example, the charge can be shaped by changing the shape of the charge cup or cavity. The charge cup or cavity can have a narrow distal end relative to the distal end; a diverging or converging longitudinal cross section; and/or a narrowed throat region along the longitudinal axis. The charge can be solid, e.g., like a cigarette, or hollow, e.g., by using a filler material. The pyrotechnic materials can be formed in different shapes, such as spheres, rods, plates, etc., to change the surface area to volume ratio, thereby affecting the burn rate and providing different burning characteristics. The pyrotechnic materials can be granular or pelletized.

Numerous charges can be used.

For example, the charge can be a combination of solid materials for two or more stages that includes $BKNO_3$ and CuO/5 aminotetrazole; thermite-aluminum powder and $FeO_2$; sulfur/chlorate mixtures; aluminum powders and potassium chlorate or potassium perchlorate; urazole and $KClO_4$; or urazole and $KNO_3$.

Other examples of charges include a system having solid and liquid materials. Examples include vinegar and sodium bicarbonate; $NaMnO_4$ (permanganate) and hydrogen peroxide; Na metal and water; Li metal and water; and quick lime and water. This system can also be used as a percussive detonator in which the $NaMnO_4$ is used to catalyze the rapid breakdown of hydrogen peroxide if greater than 70%. Establishing first and second stages for a charge could be implemented by physical segmentation of two reaction chambers, or in having a more soluble outer zone of solid reactant, and an inner zone of less soluble phase to slow the reaction. This can be accomplished by compounding and pelletizing.

Other examples of charges include a system having liquid-liquid materials. While sometimes referred to as hypergolic, or hypergol fuels, these systems could be packaged in separate containers. When the containers are physically breached, they react quickly. Examples include monomethyl hydrazine and nitrogen tetra oxide, Aerozine-50, and Competitive Impulse, Non-Carcinogenic Hypergol or CINCH, which can be an all-purpose replacement for a wide variety of hydrazine and hydrazine-based fuels.

In some embodiments, physical contact is used as the principal ignition mechanism. An igniter is pressed into direct contact with a secondary reactive material such as a propellant. When this type of configuration is employed, it is sometimes referred to as a "first-fire composition". In some cases, the "first-fire" includes a mixture, such as 50/50, of the ignition mix and the material that it is intended to ignite.

Examples of granular or pelletized igniter compositions are: $BKNO_3$ (Boron/Potassium Nitrate); ALCLO (Aluminum/Potassium Perchlorate); MAG-TEF (Magnesium/Teflon); MTV (Magnesium/Teflon/Viton); BP (Black Powder). Examples of igniter compositions utilized in "first-fire" mixes are: A1A (Iron Oxide/Diatomaceous Earth/Zirconium; ZPPV (Zirconium/Potassium Perchlorate/Viton); TiCuO (Titanium/Copper Oxide); BBC (Boron/Barium Chromate); BCC (Boron/Calcium Chromate); BBCTiPP (Boron/Barium Chromate/Titanium/Potassium Perchlorate).

While the use of a charge in connection with certain injection systems has been described above, the invention is not so limited. In general, the charges described herein can be used in any injection system (e.g., any needleless injector) properly configured to house such charges (e.g., having an appropriate charge cup or cavity).

Various combinations of charge materials can be used.

The following examples are illustrative and not intended to be limiting.

EXAMPLES

In some embodiments, a charge includes a propellant material, here, 5-AT, and a trigger material, here, a mixture of $KClO_3$ and sucrose. The charge is placed in a closed finite volume, such as a charge cavity. The propellant material (5-AT) is placed on the bottom of the charge cavity, and the trigger material is placed on the propellant material. The propellant and/or trigger material can be compacted, e.g., about 50-250 psi, or minimally packed. The trigger material can be activated, for example, by passing a current through a wire filament or using concentrated sulfuric acid. One or more other materials, such as a passive decay material (e.g., gum arabic) or a heat generating material (e.g., $B/KNO_3$) can be placed between the propellant and the trigger materials, depending on the desired pressure profile.

Figure 39:
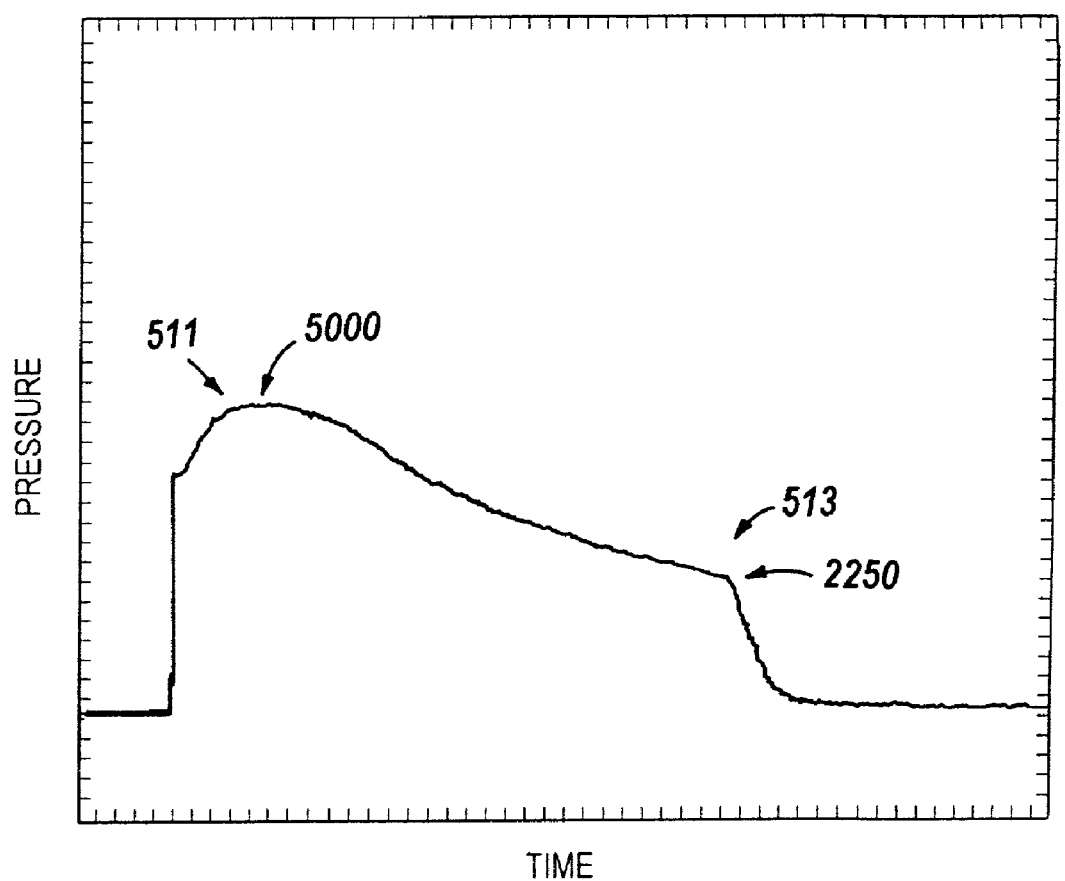
FIG. 39 is a plot of pressure as a function of time for an embodiment of a charge.

FIG. 39 shows a pressure profile (pressure as a function of time) capable of providing a needleless injection, e.g., with minimized discomfort. The pressure profile was produced by a charge of 50 mg of 5 AT, compacted under 200 psi, and 33 mg of a mixture of $KClO_3$ and sucrose (22 mg $KClO_3$ and 11 mg of sucrose) over the 5AT. The charge cavity had a diameter of about 3/16 inch. The depth, i.e., the distance between the open distal end of the charge cavity and distal end of the charge, was about 0.191 inch.

The pressure profile generally increases rapidly, e.g., over about 2-3 msec, to a peak pressure 511. The pressure then decreases to a tail pressure 513. The peak pressure can decrease to the tail pressure relatively flatly to produce a plateau region 515 with a plateau pressure. In some embodiments, the peak pressure can decrease relatively sharply, e.g., approximately exponential. It is believed that the peak pressure creates an opening, e.g., in the subject, through which injectable material can be delivered, and the plateau pressure maintains the opening so that injectable material can be continued to be delivered, e.g., without the opening closing and injectable material leaking back.

Without wishing to be bound by theory, it is believed that the pressure profile is a function of one or more parameters or variables. By adjusting these parameters or variables, the pressure profile can be adjusted to provide a desired pressure profile. For example, the pressure profile can be adjusted to inject subjects with different tissue structure, to inject different types of tissue on a subject, or to inject different types of injectable materials. Some of these variables include the amounts of components, e.g., the trigger or the propellant material, that form the charge; the compositions of the components of the charge; the degree of compaction of the components in the charge cavity, e.g., the apparent density of the components; the depth; and the void volume of the charge cavity. The void volume is approximately equal to the difference between the volume of the charge cavity and the total volume of the components of the charge. In some embodiments, the void volume is the empty volume between the trigger material and the distal end of the charge cavity, e.g., where the burst membrane is positioned.

Generally, the amount of trigger material is proportional to the peak pressure and the tail pressure. For example, increasing the amount of trigger material can increase the peak pressure and the tail pressure. Similarly, the amount of propellant material is related to the plateau pressure and the tail pressure. For example, increasing the amount of propellant material, such as 5 AT, increases the plateau pressure and the tail pressure.

The degree of compaction affects the shapes of the pressure profile curve. High compaction can produce a plateau-shaped curve. Low or minimal compaction can produce a curve that is not plateau-shaped, e.g., one that decreases in an exponential-like manner.

Figure 40:
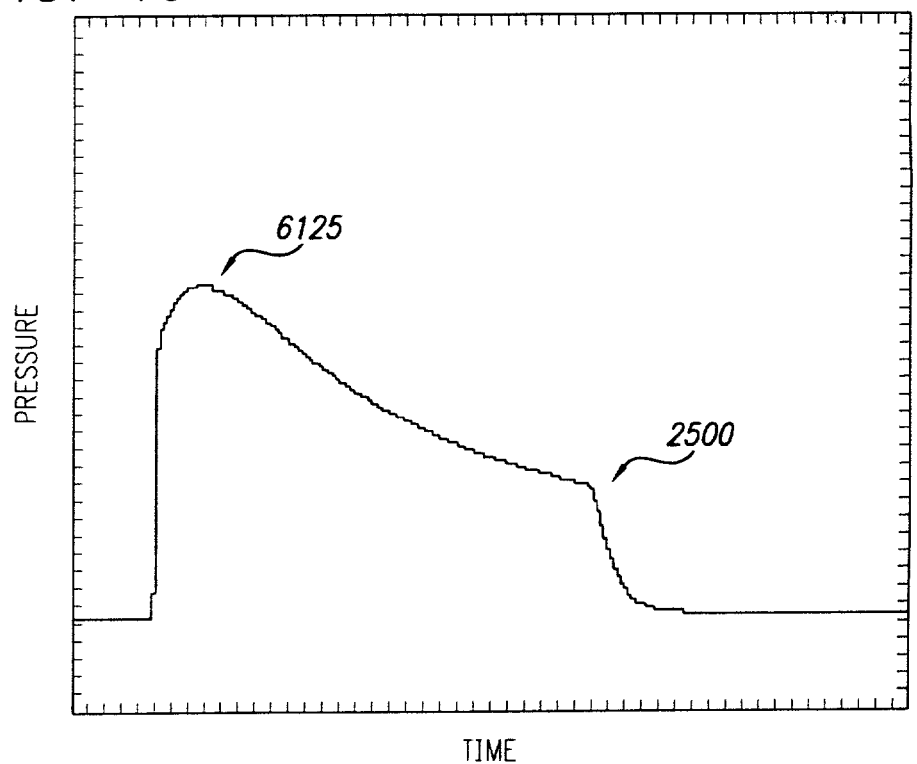
FIG. 40 is a plot of pressure as a function of time for an embodiment of a charge.

FIG. 40 shows a pressure profile for a charge having 50 mg of 5-AT (compacted by hand packing) and 39 mg of a trigger mixture (26 mg of $KClO_3$ and 13 mg of sucrose). The depth was 0.190 inch. Compared to FIG. 39, hand packing, i.e., lower compaction, of the propellant, and increasing the amount of trigger provides a relatively higher peak pressure (about 6125 psi to about 5000 psi).

Figure 41:
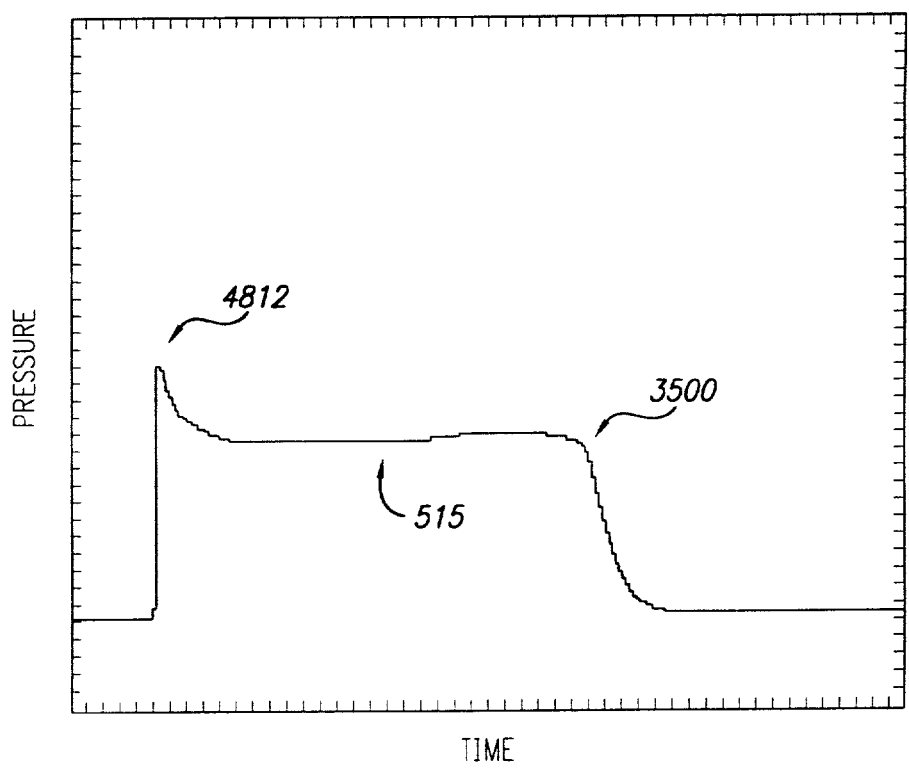
FIG. 41 is a plot of pressure as a function of time for an embodiment of a charge.

FIG. 41 shows a pressure profile for a charge having 50 mg of 5-AT (compacted under 210 psi) and 39 mg of a trigger mixture (26 mg of $KClO_3$ and 13 mg of sucrose). The depth was 0.190 inch. Compared to FIG. 40, the degree of compaction is higher. As a result, the peak pressure is lowered (about 6125 psi to about 4812 psi), but the tail pressure is increased (about 2500 psi to about 3500 psi).

Figure 42:
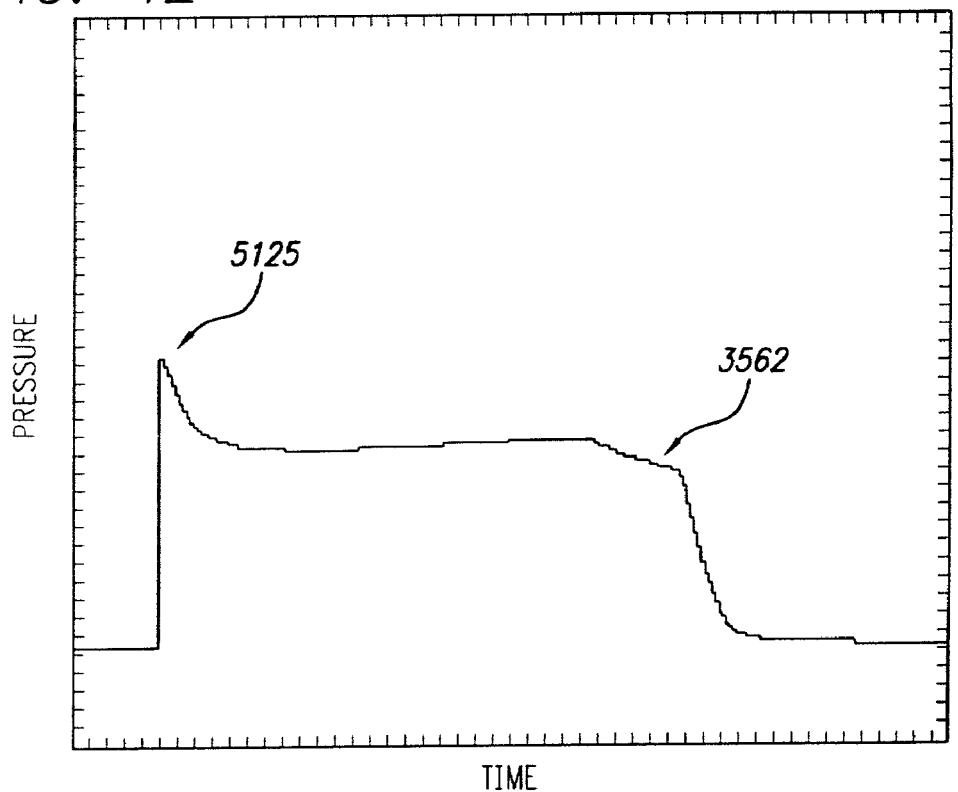
FIG. 42 is a plot of pressure as a function of time for an embodiment of a charge.

FIG. 42 shows a pressure profile for a charge having 50 mg of 5-AT (compacted under 220 psi) and 39 mg of a trigger mixture (26 mg of $KClO_3$ and 13 mg of sucrose). The depth was 0.190 inch. Compared to FIG. 41, the degree of compaction is higher, which increases injection time, i.e., the time it takes for the pressure profile to decrease from the peak pressure to the tail pressure.

Figure 43:
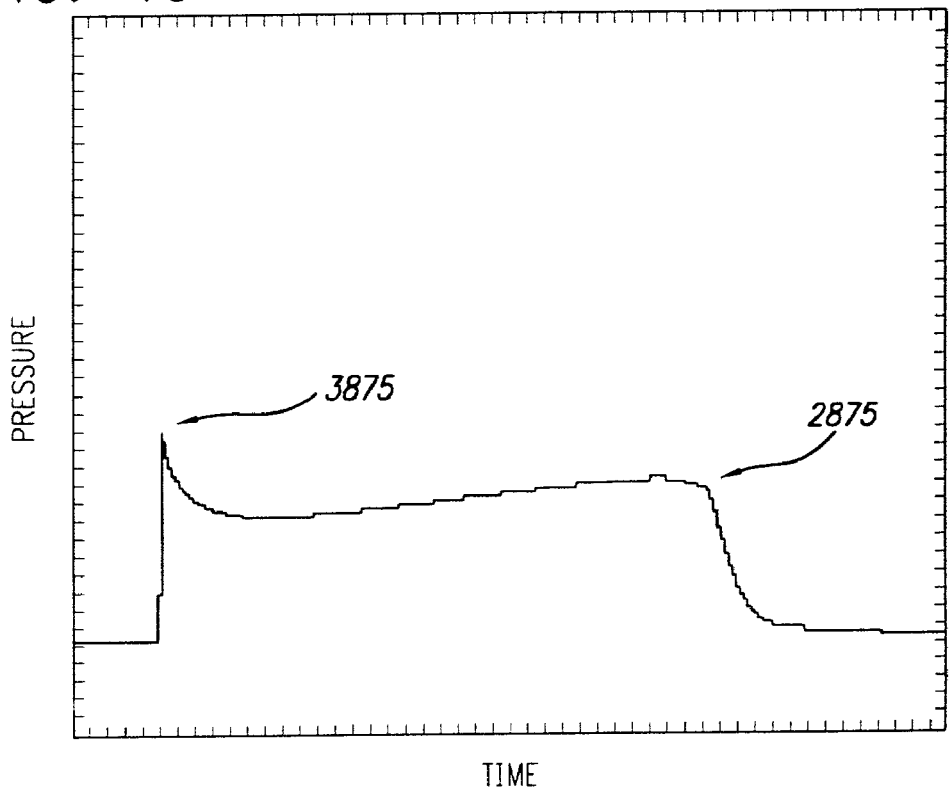
FIG. 43 is a plot of pressure as a function of time for an embodiment of a charge.

FIG. 43 shows a pressure profile for a charge having 50 mg of 5-AT (compacted under 220 psi) and 31.5 mg of a trigger mixture (21 mg of $KClO_3$ and 10.5 mg of sucrose). The depth was 0.250 inch. Compared to FIG. 42, lowering the amount of trigger material and increasing the depth, lowers the peak pressure (from about 5125 psi to about 3875 psi) and increases the injection time.

Figure 44:
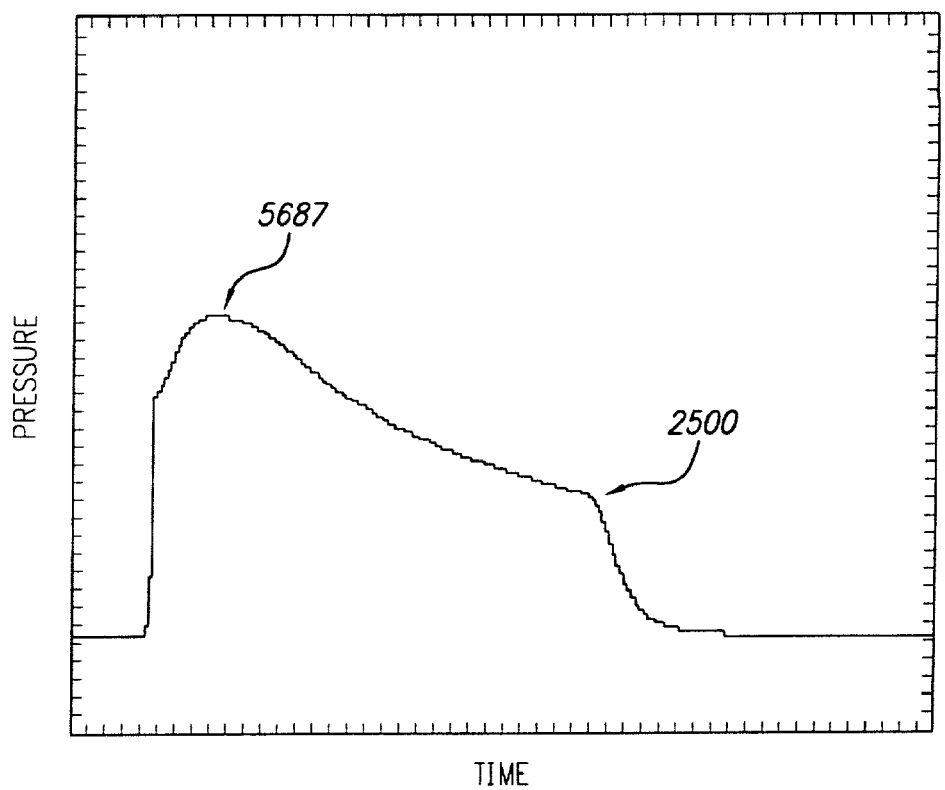
FIG. 44 is a plot of pressure as a function of time for an embodiment of a charge.

FIG. 44 shows a pressure profile for a charge having 50 mg of 5-AT (compacted under 50 psi) and 36 mg of a trigger mixture (24 mg of $KClO_3$ and 12 mg of sucrose). The depth was 0.190 inch. Compared to FIG. 39, increasing the amount of trigger material and decreasing the degree of compaction, increases the peak pressure (from about 5000 psi to about 5687 psi) and tail pressure (from about 2250 psi to about 2500 psi), slightly increases the injection time.

Figure 45:
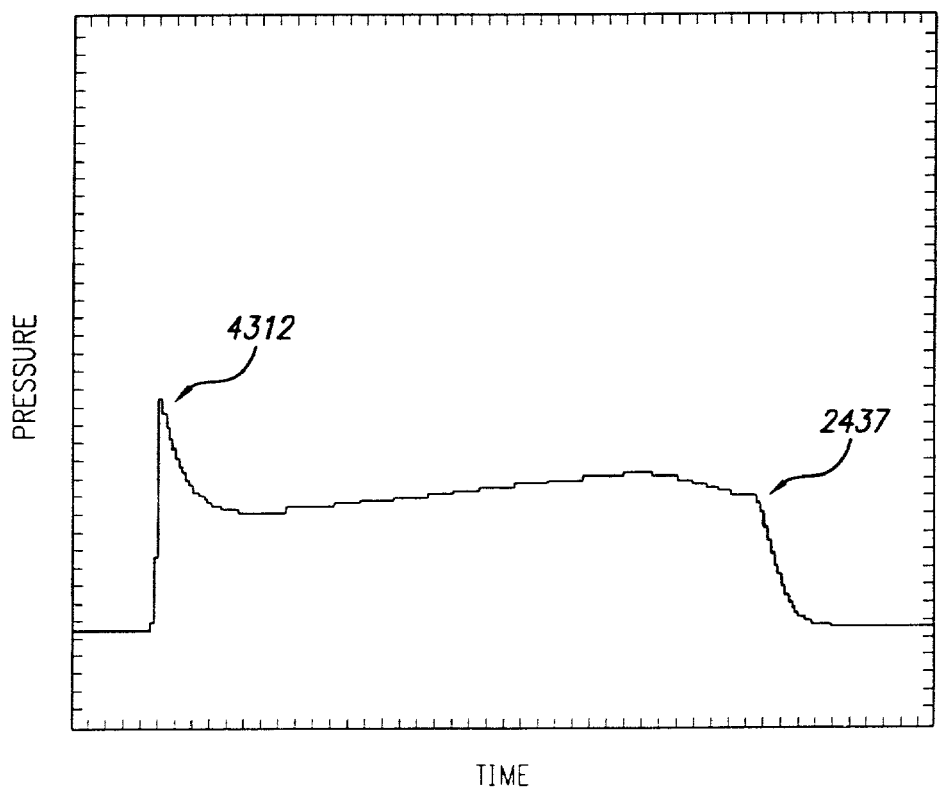
FIG. 45 is a plot of pressure as a function of time for an embodiment of a charge.

FIG. 45 shows a pressure profile for a charge having 50 mg of 5-AT (compacted under 100 psi) and 36 mg of a trigger mixture (24 mg of $KClO_3$ and 12 mg of sucrose). The depth was 0.190 inch. Compared to FIG. 44, increasing the degree of compaction decreases the peak pressure (from about 5687 psi to about 4312 psi) and increases the injection time.

Figure 46:
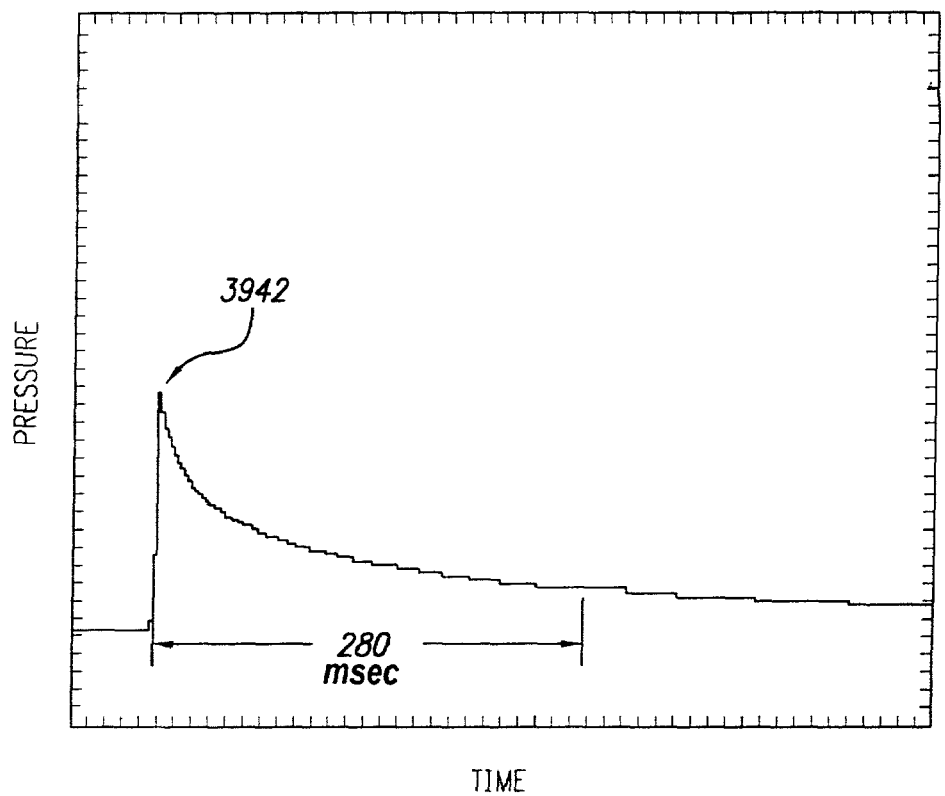
FIG. 46 is a plot of pressure as a function of time for an embodiment of a charge.

FIG. 46 shows a pressure profile for a charge having only 31.5 mg of a trigger mixture (21 mg of $KClO_3$ and 10.5 mg of sucrose). The depth was 0.070 inch. Compared to FIG. 39, removing the propellant results in a rapid decrease from the peak pressure.

In some embodiments, the charge can further include $B/KNO_3$, an example of a material capable of generating high heat and low gas, between the propellant and trigger materials. The $B/KNO_3$ is capable of further expanding gases generated by the trigger material and increasing the combustion kinetics of the propellant. Generally, the $B/KNO3$ can increase the peak pressure, the plateau pressure, and/or the tail pressure.

Figure 47:
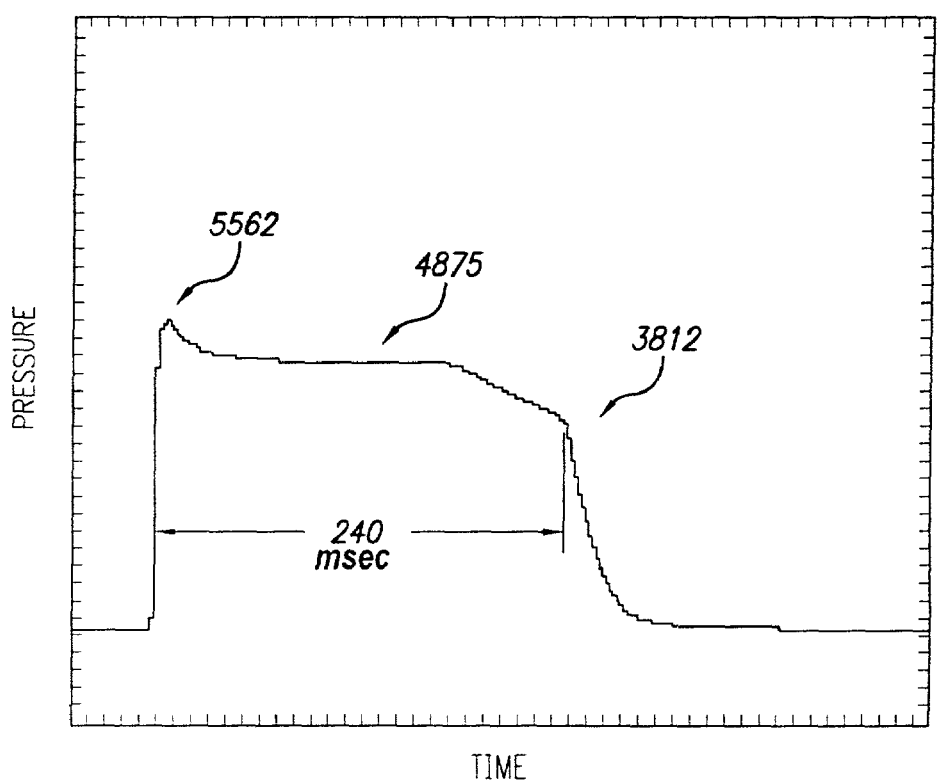
FIG. 47 is a plot of pressure as a function of time for an embodiment of a charge.

FIG. 47 shows a pressure profile for a charge having 50 mg of 5-AT (compacted under 210 psi) and 39 mg of a trigger mixture (26 mg of $KClO_3$ and 13 mg of sucrose). The depth was 0.220 inch. 20 mg of $B/KNO_3$ (compacted under 40 psi) was placed between the 5-AT and the trigger mixture. The $B/KNO_3$ generally provided a relatively high peak pressure (about 5562 psi), a relatively high plateau pressure (about 4875 psi), a relatively high tail pressure (about 3812 psi), and a relatively short injection time.

Figure 48:
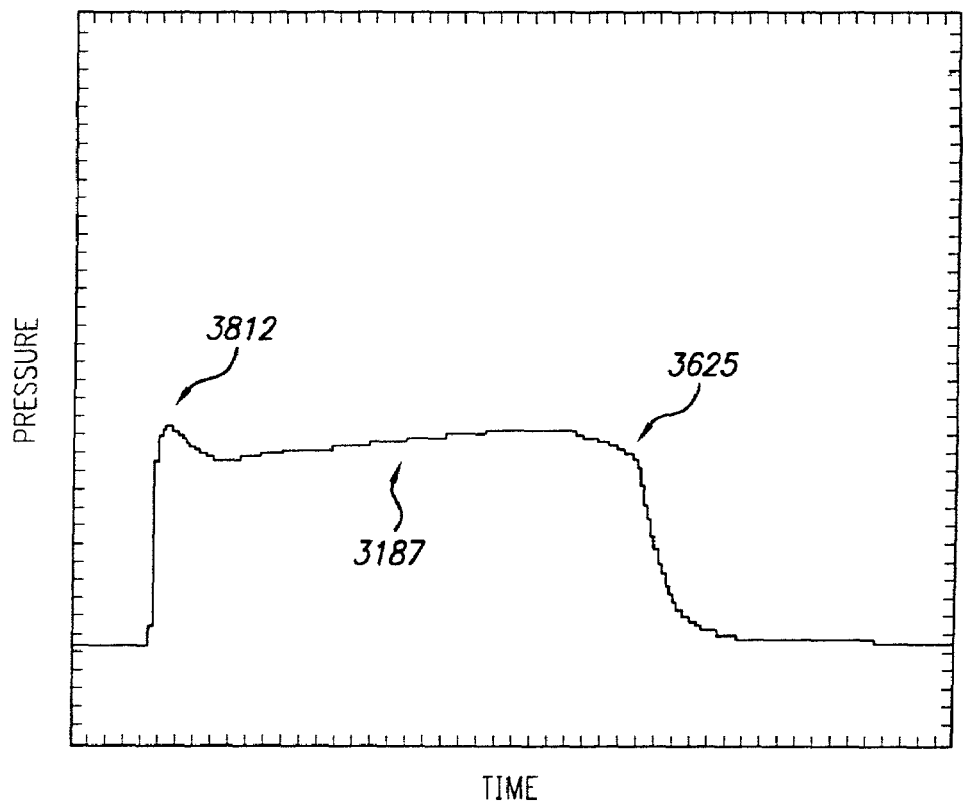
FIG. 48 is a plot of pressure as a function of time for an embodiment of a charge.

FIG. 48 shows a pressure profile for a charge having 50 mg of 5-AT (compacted under 220 psi) and 21 mg of a trigger mixture (14 mg of $KClO_3$ and 7 mg of sucrose). The depth was 0.190 inch. 20 mg of $B/KNO_3$ (compacted under 40 psi) was placed between the 5-AT and the trigger mixture. Compared to FIG. 47, a decrease in depth and the amount of trigger material lower the peak pressure (from about 5562 psi to about 3812 psi) but slightly increase the slope of the plateau region.

Figure 49:
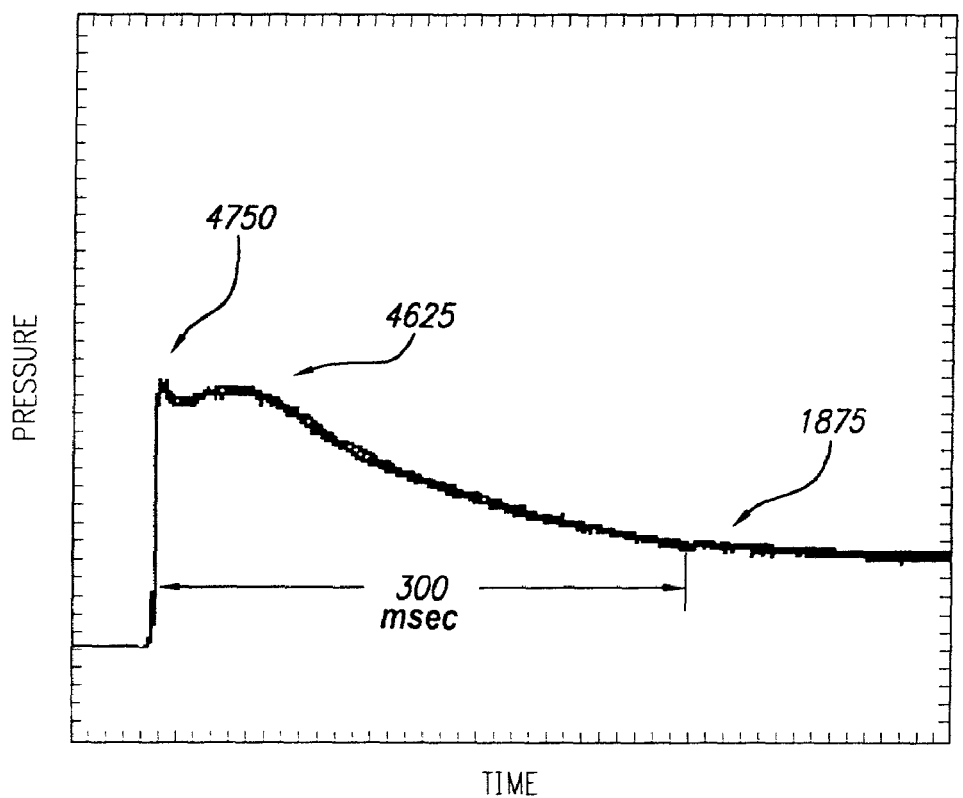
FIG. 49 is a plot of pressure as a function of time for an embodiment of a charge.
Figure 50:
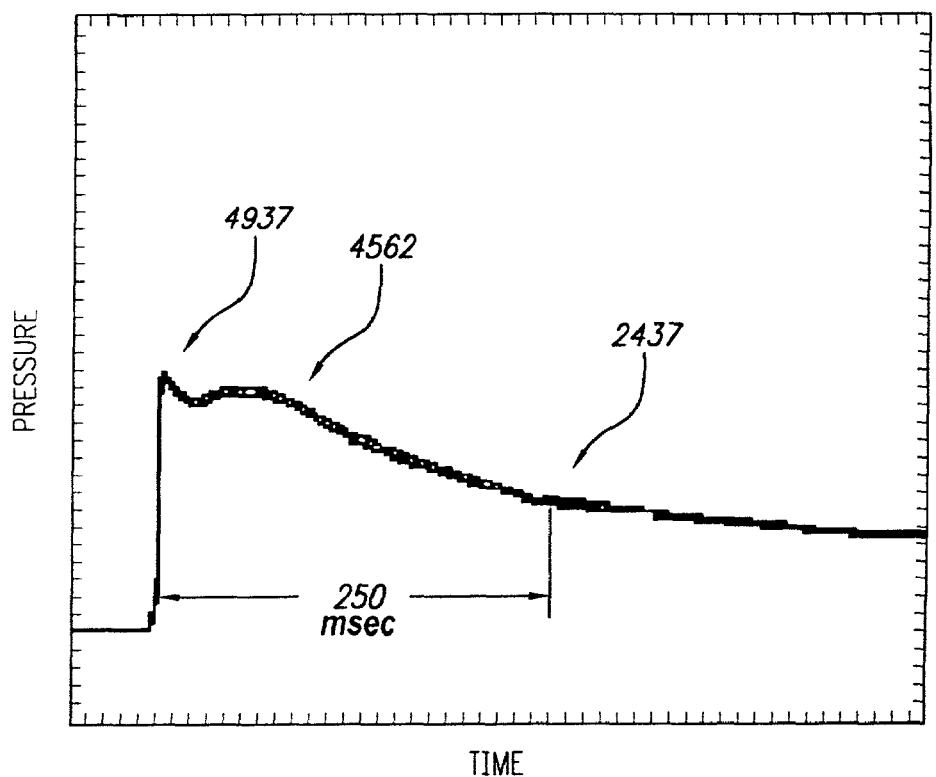
FIG. 50 is a plot of pressure as a function of time for an embodiment of a charge.
Figure 51:
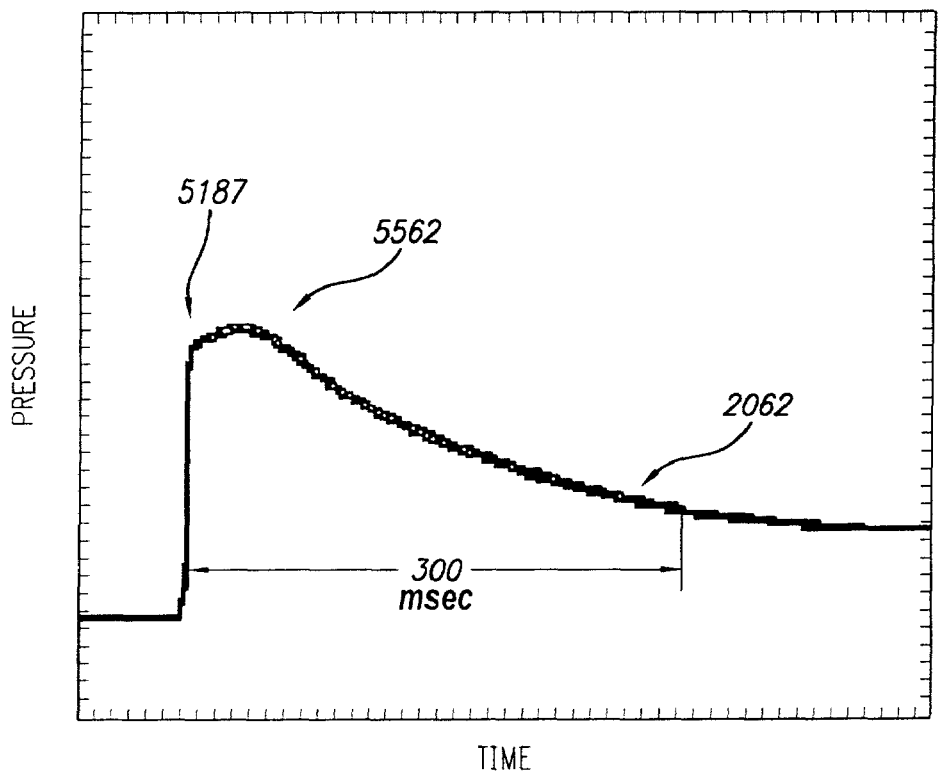
FIG. 51 is a plot of pressure as a function of time for an embodiment of a charge.
Figure 52:
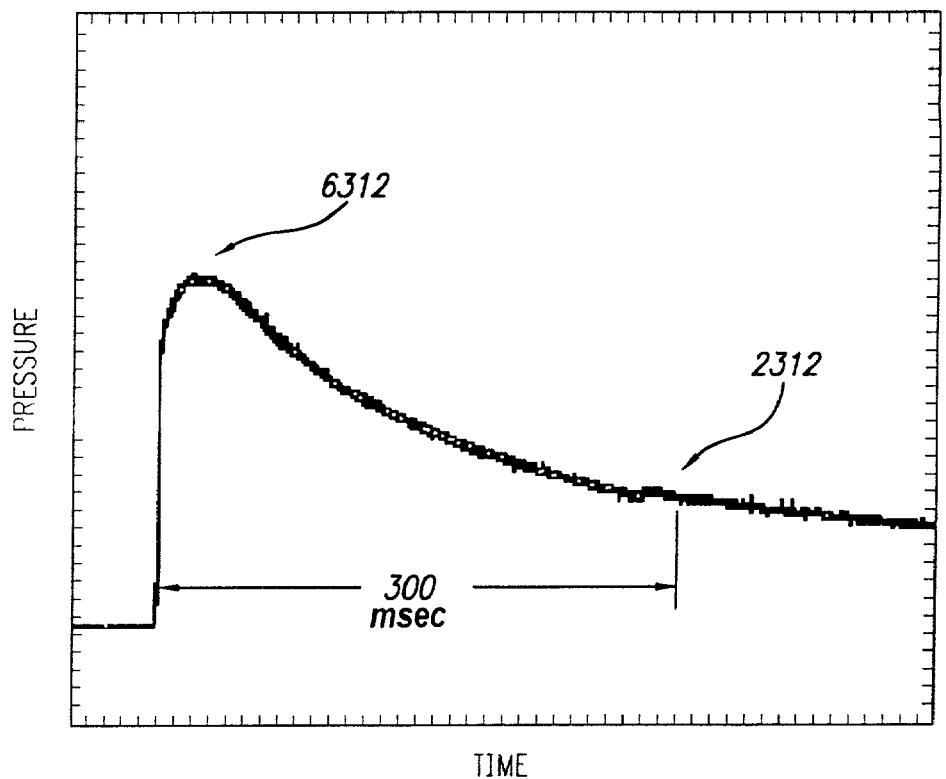
FIG. 52 is a plot of pressure as a function of time for an embodiment of a charge.
Figure 53:
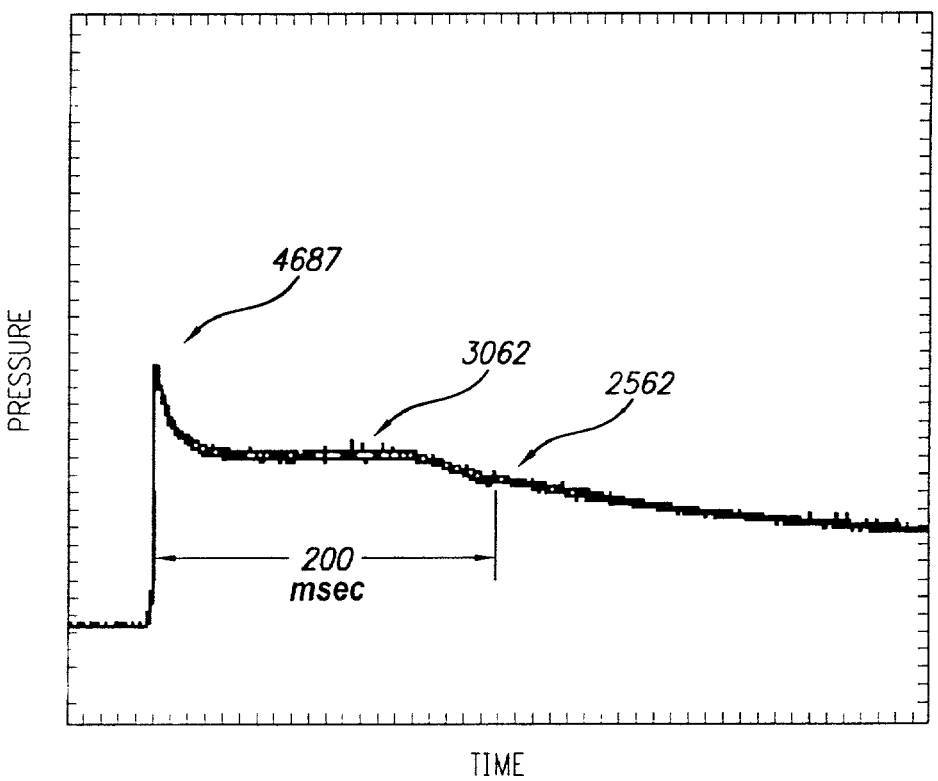
FIG. 53 is a plot of pressure as a function of time for an embodiment of a charge.
Figure 54:
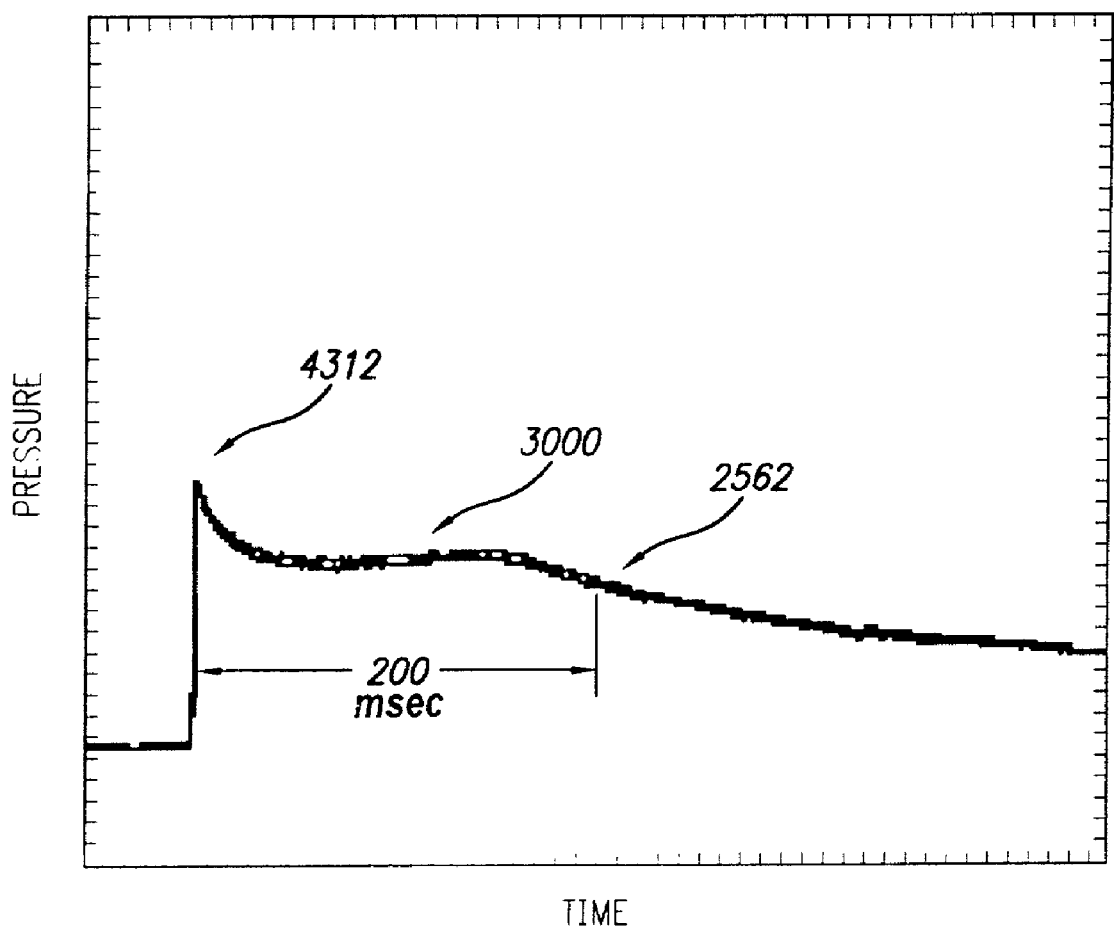
FIG. 54 is a plot of pressure as a function of time for an embodiment of a charge.

FIG. 49 shows a pressure profile for a charge having 30 mg of 5-AT (compacted under 210 psi) and 36 mg of a trigger mixture (24 mg of $KClO_3$ and 12 mg of sucrose). The depth was 0.130 inch. 10 mg of $B/KNO_3$ (compacted under 40 psi) was placed between the 5-AT and the trigger mixture. The pressure profile has a double peak with a relatively rapidly decreasing tail.

For a given charge, the pressure profile can be modified by modifying the depth. Modifying the depth can produce pressure profiles having both an approximately exponentially decaying region and a relatively flat plateau region.

FIGS. 49 to 54 show pressure profiles for a charge having 30 mg of 5-AT (compacted under 210 psi), 10 mg of $B/KNO_3$ (compacted under 40 psi), 36 mg of a trigger material mixture (24 mg of $KClO_3$ and 12 mg of sucrose). In FIG. 49 the depth was 0.130 inch; in FIG. 50, the depth was 0.135 inch; in FIG. 51 the depth was 0.145 inch; in FIG. 52, the depth was 0.155 inch; in FIG. 53, the depth was 0.165 inch; and in FIG. 54, the depth was 0.175 inch. Controlling the depth can change the shape of the pressure profile, e.g., whether the profile has a rapidly changing portion and/or a relatively flat portion.

A pressure profile can be modified, e.g., tailored, in whole or in part, by modifying one or more of the variables described above.

Other embodiments are within the claims.

What is claimed is:

1. An injection system comprising:
    an injector device having a first cavity in fluid communication with an orifice, the orifice configured for needleless injection such that a fluid contained in the first cavity can be ejected through the orifice into an injection site; and
    a fluid transfer device having a second cavity containing fluid, a proximal end coupled with the injector device proximate the orifice, a first seal and a moveable fluid passageway, the moveable fluid passageway being positioned between the first cavity and the first seal in an initial position, the fluid passageway configured to pierce the first seal in a transfer position thereby fluidly coupling the second cavity with the first cavity, the fluid transfer device being removeable from the injector device upon transfer of the fluid from the second cavity to the first cavity.

2. The injection system of claim 1, wherein the fluid transfer device includes a third cavity sealed from the second cavity by a second seal.

3. The injection system of claim 2, wherein the second seal is a first slideable stopper located between the second and third cavities.

4. The injection system of claim 3, wherein the third cavity includes a second slideable stopper having a fixed needle, second slideable stopper being spaced from the first slideable stopper and configured to move toward the first slideable stopper such that the needle pierces the second seal and fluidly couples the second and third cavities.

5. The injection system of claim 2, wherein the third cavity includes a third slideable stopper configured to pressurize the third cavity.

6. The injection system of claim 5, wherein the fluid transfer device includes a base coupled to third slideable stopper and extending from the fluid transfer device.

7. The injection system of claim 1, further comprising a charge cup in the injector device.

8. The injection system of claim 7, wherein a charge in the charge cup comprises at least two discrete materials.

9. The injection system of claim 8, wherein the at least two discrete materials have different combustion characteristics.

10. The injection system of claim 1, wherein the fluid transfer device is configured to store two injectable materials in separate compartments.

11. The injection system of claim 10, wherein one of the two injectable materials is a liquid, and the other of the two injectable materials is a lyophilized material.

12. The injection system of claim 11, wherein the injection system is configured to mix the liquid with the lyophilized material within the second cavity to form a mixture before transferring the mixture to the first cavity.

13. The injection system of claim 1, wherein the fluid passageway abuts both the orifice and the seal sealing the second cavity in the initial position.

14. The injection system of claim 1, wherein the fluid passageway is a needle.

15. The injection system of claim 1, wherein the injector device and the fluid transfer device are substantially coaxial when engaged.

16. The injection system of claim 1, wherein the injector device is comprised of a polymer and the fluid transfer device is comprised of a glass.

17. The injection system of claim 1, wherein the fluid transfer device is directly connected to the injector device when the fluid transfer device and the injector device are engaged.

18. The injection system of claim 1, wherein the moveable fluid passageway comprises a first fluid passageway adjacent to the first seal, the first seal sealing a first end of the second cavity, the second cavity configured to contain a material and a first slideable stopper having a second seal sealing a second end of the second cavity, a second fluid passageway fixed to a second slideable stopper adjacent to the second seal, the second slideable stopper spaced distally from the first slidable stopper, the second seal sealing a first end of a third cavity configured to contain the fluid and a third slideable stopper sealing a second end of the third cavity, and wherein the first fluid passageway is configured to pierce the first seal such that the first cavity is in fluid communication with the second cavity when the injector device is engaged with the fluid transfer device, the second fluid passageway is configured to pierce the second seal such that the third cavity is in fluid communication with the second cavity when the injector device and the fluid transfer device are engaged and the third slideable stopper is urged toward the injector device, the third slideable stopper is configured to urge the fluid through the second fluid passageway, mix with the material to form a fluid mixture and flow through the first fluid passageway and into the first cavity, the first and second slideable stoppers configured to move together toward the proximal end of the fluid transfer device as a volume of the second cavity reduces.

19. The injection system of claim 1, wherein the proximal end of the fluid transfer device extends outwardly past the moveable fluid passageway.

20. The injection system of claim 1, wherein moving the entire fluid transfer device toward the injection device causes the moveable fluid passageway to transition from the initial position to the transfer position.

21. The injection system of claim 1, wherein the moveable fluid passageway has a flared end proximate the proximal end of the fluid transfer device.

* * * * *